United States Patent [19]

Baxter et al.

[11] Patent Number: 5,348,978
[45] Date of Patent: Sep. 20, 1994

[54] ANGIOTENSIN CONVERTING ENZYME INHIBITORS

[75] Inventors: Andrew J. G. Baxter, Nottingham; Premji Meghani, Leicestershire, both of England

[73] Assignee: Fisons plc, Ipswich, England

[21] Appl. No.: 956,877

[22] PCT Filed: Jun. 18, 1991

[86] PCT No.: PCT/GB91/00980

§ 371 Date: Dec. 10, 1992

§ 102(e) Date: Dec. 10, 1992

[87] PCT Pub. No.: WO92/00276

PCT Pub. Date: Jan. 9, 1992

[30] Foreign Application Priority Data

Jun. 22, 1990 [GB] United Kingdom .................. 9013994
Oct. 2, 1990 [GB] United Kingdom .................. 9021411
Apr. 6, 1991 [GB] United Kingdom .................. 9107237

[51] Int. Cl.⁵ .................... A61K 31/25; A61K 31/38; C07C 321/08; C07D 333/34
[52] U.S. Cl. ..................... 514/547; 549/66; 560/147; 514/445
[58] Field of Search ............... 560/147; 514/547, 445; 549/66

[56] References Cited

U.S. PATENT DOCUMENTS 4,242,265 12/1980 Wade et al. .................. 260/326
4,611,002 9/1986 Ondetti .................. 514/547

FOREIGN PATENT DOCUMENTS 2001963 2/1979 United Kingdom .

OTHER PUBLICATIONS

Carey et al. Advanced Organic Chemistry, Part B: Reactions & Synthesis, N.Y., Plenum Press, 1990 pp. 677–678.

*Primary Examiner*—Richard L. Raymond
*Assistant Examiner*—M. Cebulak
*Attorney, Agent, or Firm*—Marshall, O'Toole, Gerstein, Murray & Borun

[57] ABSTRACT

Angiotensin converting enzyme inhibitors have the formula $Z(CH_2)_nCHR_1COOCHR_2COOH$
in which Z is $-SR_3$, $-COCHR_4NHCOR_5$,

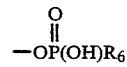

or $-NHCHR_7COOH$, $R_4$, $R_5$, $R_6$, and $R_7$, which may be the same or different, are each phenyl or alkylphenyl $C_{7-12}$, $R_4$ is hydrogen, alkyl $C_{1-6}$, $NHR_8$ or $(CH_2)_pR_9$, $R_2$ is $(CH_2)_mXR_{10}$, alkyl $C_{1-6}$ optionally substituted by a saturated 5- or 6-membered carbocyclic or heterocyclic ring, alkylhalo $C_{1-6}$, alkylcyano $C_{1-6}$, or alkyl phenyl $C_{7-12}$, the phenyl being optionally substituted by $NO_2$ or $NH_2$, X is O, $S(O)_q$, C=O or $NR_{11}$, and $R_{10}$ is alkyl $C_{1-6}$, alkylhalo $C_{1-6}$, alkoxy $C_{1-6}$, alkoxy $C_{1-6}$ substituted by halogen, alkanoyl $C_{1-6}$, $S(O)_rR_{12}$, $NR_{13}R_{14}$, phenyl, alkylphenyl $C_{7-12}$, naphthalenyl or a 5-membered unsaturated heterocyclic ring, n is an integer from 0 to 6, m and p, which may be the same or different, are each an integer from 1 to 6, $R_9$ is hydrogen, $SR_{15}$ or phenyl optionally substituted by $OR_{16}$, $R_3$ and $R_{15}$, which may be the same or different, are each hydrogen or alkanoyl $C_{1-6}$, $R_8$ is hydrogen or $COOR_{17}$, q and r, which may be the same or different, are each 0, 1, or 2, $R_{11}$, $R_{13}$, $R_{14}$, $R_{16}$, and $R_{17}$, which may be the same or different, are each hydrogen or alkyl $C_{1-6}$, and $R_{12}$ is hydrogen, alkyl $C_{1-6}$ or phenyl.

The compounds, and salts thereof, are useful as vasodilators.

7 Claims, No Drawings

ANGIOTENSIN CONVERTING ENZYME INHIBITORS

This invention relates to new compounds, methods for their preparation and compositions containing them.

A wide variety of angiotensin converting enzyme (ACE) inhibitors are known, e.g. from British Patent No: 2001963B.

According to the invention we provide compounds of formula I, $$Z(CH_2)_n CHR_1 COOCHR_2 COOH \qquad I$$

in which Z is $-SR_3$, $-COCHR_4NHCOR_5$, $$-O\overset{O}{\underset{\|}{P}}(OH)R_6$$

or $-NHCHR_7COOH$, $R_4$, $R_5$, $R_6$ and $R_7$, which may the same or different, are each phenyl or alkylphenyl $C_{7-12}$, $R_1$ is hydrogen, alkyl $C_{1-6}$, $NHR_8$ or $(CH_2)_p R_9$, $R_2$ is $(CH_2)_m XR_{10}$, alkyl $C_{1-6}$ optionally substituted by a saturated 5- or 6-membered carbocyclic or heterocyclic ring, alkylhalo $C_{1-6}$, alkylcyano $C_{1-6}$, or alkyl phenyl $C_{7-12}$, the phenyl being optionally substituted by $NO_2$ or $NH_2$, X is O, $S(O)_q$, C=O or $NR_{11}$, and $R_{10}$ is alkyl $C_{1-6}$, alkylhalo $C_{1-6}$, alkoxy $C_{1-6}$, alkoxy $C_{1-6}$ substituted by halogen, alkanoyl $C_{1-6}$, $S(O)_r R_{12}$, $NR_{13}R_{14}$, phenyl, alkylphenyl $C_{7-12}$, naphthalenyl or a 5-membered unsaturated heterocyclic ring, n is an integer from 0 to 6, m and p, which may be the same or different, are each an integer from 1 to 6, $R_9$ is hydrogen, $SR_{15}$ or phenyl optionally substituted by $OR_{16}$, $R_3$ and $R_{15}$, which may be the same or different, are each hydrogen or alkanoyl $C_{1-6}$, $R_8$ is hydrogen or $COOR_{17}$, q and r, which may be the same or different, are each 0, 1 or 2, and $R_{11}$, $R_{12}$, $R_{13}$, $R_{14}$, $R_{16}$ and $R_{17}$, which may be the same or different, are each hydrogen or alkyl $C_{1-6}$, provided that when Z is $SR_3$, n is 1 and $R_1$ is hydrogen or alkyl $C_{1-6}$, then $R_2$ is not alkyl $C_{1-6}$ or alkylphenyl $C_{7-12}$, and pharmaceutically acceptable salts thereof.

According to the invention we also provide a process for the production of a compound of formula I, or a pharmaceutically acceptable salt thereof which comprises a) reacting a compound of formula II, or a salt or ester thereof, $$Z(CH_2)_n CHR_1 COL_a \qquad II$$

in which Z, $R_1$ and n are as defined above, and $L_a$ is a good leaving group, with a compound of formula III, or a salt or ester thereof, $$HOCHR_2 COOH \qquad III$$

in which $R_2$ is as defined above, b) removal of a protecting group from a corresponding protected compound of formula I in which one or more of the functional groups is protected, and where desired or necessary converting a compound of formula I, or another salt thereof, to a pharmaceutically acceptable salt thereof or vice versa.

In process a) the good leaving group $L_a$ may be, for example, halogen and the reaction may be carried out in an inert solvent, e.g. dichloromethane at a temperature of from about 0° to 100°. When $L_a$ is halogen the reaction may be carried out in the presence of base, e.g. pyridine.

The reaction may comprise the formation of, optionally in situ, an activated derivative of an acid, e.g. an anhydride, a dicyclohexylcarbodiimide or a carbodiimidazole derivative. The reaction may be carried out in a solvent which is inert under the reaction conditions, e.g. dichloromethane or ethyl acetate, at a temperature of from $-10°$ C. to the boiling point of the solvent, preferably from 0° C. to 30° C. The reaction may be carried out in the presence of a base, e.g. triethylamine. When the reaction involves dicyclohexylcarbodiimide it may be carried out in the presence of an activating agent, e.g. hydroxybenzotriazole or 4-(dimethylamino)pyridine.

The reaction will of course vary with the particular activated derivative used.

In process b) the functional group which is protected may be an amino, thiol or carboxylic acid group. The protecting group can be any convenient protecting group conventionally used in peptide synthesis and may be removed using techniques conventionally used in peptide synthesis. Thus protecting groups which may be used are alkoxy $C_{1-6}$, which may be a straight chain or branched alkoxy, e.g. 2-propenyloxy or t-butyloxy; phenylalkoxy $C_{7-12}$, e.g. benzyloxy; or alkanoyl $C_{2-7}$, e.g. acetyl. These groups can be removed by hydrolysis, for example basic hydrolysis, e.g. using aqueous methanolic sodium or potassium hydroxide or aqueous ammonia solution; or cleavage using, for example, trifluoroacetic acid; or by hydrogenation, e.g. using palladium on charcoal. Amino-protecting groups which may be mentioned include alkyloxycarbonyl $C_{2-7}$, e.g. t-butyloxycarbonyl, or phenylalkyloxycarbonyl $C_{8-13}$, e.g. benzyloxycarbonyl.

Salts of the compounds of formula I may be formed by reacting the free acid, or a salt thereof, or the free base, or a salt or derivative thereof, with one or more equivalents of the appropriate base or acid. The reaction may be carried out in a solvent or medium in which the salt is insoluble or in a solvent in which the salt is soluble, e.g. ethanol, tetrahydrofuran or diethyl ether, which may be removed in vacuo, or by freeze drying. The reaction may also be a metathetical process or it may be carried out on an ion exchange resin.

Pharmaceutically acceptable salts of the compounds of formula I include ammonium salts, alkali metal salts, e.g. sodium and potassium salts; alkaline earth metal salts, e.g. the calcium and magnesium salts; salts with organic bases, e.g. N-methyl-D-glucamine; and salts with amino acids, e.g. with arginine, lysine etc. Also, when the molecule contains a basic group, salts with organic or inorganic acids, e.g. with HCl, HBr, $H_2SO_4$, methanesulphonic, toluenesulphonic, maleic, fumaric or camphorsulphonic acids. The non-toxic physiologically acceptable salts are preferred, although other salts are also useful, e.g. in isolating or purifying the product.

Preferred organic bases included dicyclohexylamine and adamantanamine.

Preferred organic acids include trifluoroacetic acid.

The compounds of formula II and III are either known or may be made by conventional processes known per se, e.g. as described in U.S. Pat. Nos.: 4,053,651 and 4,105,776.

The starting materials for all of the above processes are either known or may be made from compounds using conventional processes known per se.

The compounds of formula I, and the intermediates thereof, may be isolated from their reaction mixtures using conventional techniques known per se.

The processes described above may produce the compound of formula I or a derivative thereof. It is also within the scope of this invention to treat any derivative so produced to liberate the free compound of formula I, or convert one derivative into another.

In addition to the processes described above the compounds of formula I may be made by a variety of processes which are analogous to those known for the production of structurally similar compounds.

By the term alkyl we mean straight, branched or cyclic saturated or unsaturated alkyl groups.

The compounds of formula I may contain one or more asymmetric carbon atoms and may therefore exhibit optical and/or disatereoisomerism. Diastereoisomers may be separated using conventional techniques, e.g. chromatography or fractional crystallisation. The various optical isomers may be isolated by separation of a racemic or other mixture of the compounds using conventional, e.g. fractional crystallisation or HPLC, techniques. Alternatively the desired optical isomers may be made by reaction of the appropriate optically active starting materials under conditions which will not cause racemisation.

The compounds of formula I in which the COOH group is protected are also useful as intermediates for the preparation of compounds of formula I.

We prefer compounds of formula I in which $R_1$ is methyl.

We prefer compounds in which $R_2$ is $(CH_2)_m XR_{10}$.

X is preferably S or O.

$R_{10}$ is preferably alkyl, particularly methyl, ethyl, i-propyl or t-butyl.

$R_3$ is preferably acetyl or more preferably hydrogen.

We prefer compounds in which n is 1.

We prefer compounds in which m is 1.

The compounds of the invention are advantageous in that they are more efficacious, produce fewer side effects, are shorter acting, more readily absorbed, less toxic, distributed in the body tissues in a different manner or have other advantageous properties when compared to compounds of similar structure.

The compounds of the invention are useful because they posses pharmacological properties. In particular they inhibit angiotensin converting enzyme and thus block conversion of the decapeptide angiotensin I to angiotensin II (see Example X). Angiotensin II is a potent vasoconstrictor in mammals. Angiotensin II stimulates aldosterone release which results in salt and fluid retention, it is pro-arrhythmic and exacerbates damage due to myocardial infarction. Inhibitors of angiotensin converting enzyme are thus effective vasodilators in a variety of animal models (see Example Y) and are indicated for use clinically, for example, in patients with acute myocardial infarction, acute heart failure or hypertension. See, for example, D. W. Cushman et al, *Biochemistry*, 1977, 16, 5484; E. W. Petrillo and M. A. Ondetti, *Med. Res. Rev.*, 1982, 2, 93; or H. M. McAlpine, J. J. Morton, B. Leckie and H. J. Dargie, *J. Cardiavas. Pharmacol.*, 1987, 9 (Suppl 2), S25-S30.

Thus, the compounds of the invention are useful as vasodilators in treating heart failure, renal failure, hypertension, angina pectoris and ischaemic heart disease in mammals, including humans and they can be utilised to achieve vasodilation, e.g. in formulations containing appropriate pharmaceutically acceptable excipients, diluents or carriers. The compounds of the invention can be administered (to animals or humans) by a variety of routes, e.g. sublingually or intramuscularly and especially intravenously at dosages of 1 mg to 10 g per hour for several hours, to a total daily dose of 60 g per day. The dose will vary depending on the type and severity of disease, weight of patient and other factors which a person skilled in the art will recognise.

Thus according to the invention we provide the first pharmaceutical use of a compound of formula I. We provide a compound of formula I for use as a medicament. In particular we provide the use of a compound of formula I in the manufacture of a medicament for the treatment of heart failure. We further provide the use of a compound of formula I in the manufacture of a medicament for the treatment of any of the following conditions; heart failure, renal failure, hypertension, angina pectoris and ischaemic heart disease.

The compounds of this invention may be given in combination with other pharmaceutically active compounds, e.g. diuretics, thrombolytics or antihypertensives. The dosage of the other pharmaceutically active compound can be that conventionally used when the compound is administered on its own, but is preferably somewhat lower. To illustrate these combinations, one of the vasodilators of this invention can be combined at levels ranging, e.g. from 1 mg to 60 g per day with the following antihypertensives and diuretics in dose ranges per day as indicated:

hydrochlorothiazide (15–200 mg), chlorothiazide (125–2000 mg), ethacrynic acid (15–200 mg), amiloride (5–20 mg), furosemide (5–600 mg), atenolol (5–100 mg), propanolol (20–640 mg), verapamil (120–480 mg) and methyldopa (65–2000 mg). In addition, the triple drug combinations of hydrochlorothiazide (15–200 mg) plus amiloride (5–20 mg) plus converting enzyme inhibitor of this invention (1 mg–60 g) or hydrochlorothiazide (15–200 mg) plus timolol (5–50 mg), plus the converting enzyme inhibitor of this invention (1 mg–60 g) are contemplated. The following compounds may also be combined; inotropes,e.g. amrinone (5 $\mu$g–600 mg; enoximone (5 $\mu$g–600 mg); vasodilators, e.g. nitroglycerine (1–15 mg), isosorbide (1–150 mg), sodium nitroprusside (1–600 mg); inotropic vasodilators, e.g. dopamine (1–50 mg), dobutamine (1–50 mg), dopexamine (1–1000 mg); osmotic diuretics, e.g. mannitol (50–200 mg); anti-arrhythmics, e.g. procainamide (1–1000 mg); thrombolytics, e.g. streptokinase (100,000–600,000 IU); opioid analgesics, e.g. butorphanol, codeine, diamorphine (1–5 mg), methadone; antibiotics, e.g. sulphonamide, tetracyclines, penicillins; analgesics, e.g. aspirin (1–1000 mg), electrolytes, e.g. sodium, potassium, magnesium; acids and bases, e.g. sodium bicarbonate, ammonium chloride, citric acid, sodium citrate.

The above dose ranges may be adjusted on a unit basis as necessary to permit divided daily dosage. Also, the dose may vary depending on the severity of the disease, weight of patient and other factors which a person skilled in the art will recognise.

According to our invention we also provide a pharmaceutical composition comprising preferably less than 80%, more preferably less than 50%, e.g. 0.1 to 20%, by weight of a compound of formula I, or a pharmaceutically acceptable salt thereof, in admixture with a pharmaceutically acceptable adjuvant, diluent or carrier.

Thus, the compound may be put up as a tablet, capsule, dragee, suppository, suspension, solution, injection, e.g. intravenously, intramuscularly or intraperitoneally, implant, a topical, e.g. transdermal, preparation such as a gel, cream, ointment, aerosol or a polymer system, or an inhalation form, e.g. an aerosol or a powder formulation.

We prefer compositions which are designed to be taken intravenously as a continuous infusion or bolus injection. Thus we prefer a solution which may, for example, be made by dissolution of the compound in an appropriate vehicle, e.g. an isotonic glucose or dextrose solution.

Certain of the compounds of formula I can form hydrates or solvates, for example, with an alcohol such as ethanol.

The invention will now be illustrated by the following Examples in which temperatures are in degrees Celsius.

EXAMPLE 1

2(R)-(3-Mercapto-2(S)-methyl-1-oxopropoxy)-3-(methylthio)propanoic acid 1-adamantanamine salt a) (R)-2-Hydroxy-3-(methylthio)propanoic acid Sodium methanethiolate (0.67 g, 9.57 mmol) was added at 25° to a solution of (R)-3-chloro-2-hydroxypropanoic acid (0.3 g, 2.41 mmol) in methanol (20 ml). The reaction mixture was heated at reflux for 8 h, then cooled to room temperature. The precipitate was removed by filtration and the filtrate was evaporated. The residue was acidified to pH 2 with dilute hydrochloric acid and extracted with ethyl acetate. The organic extract were dried ($Na_2SO_4$) and the solvent evaporated to give the sub-title compound (0.32 g).

nmr $\delta(CDCl_3)$ 2.19 (3H, s), 2.90 (1H, dd), 3.05 (1H, dd), 4.47 (1H, dd);

m/z 280 (M+ for DiTMS).

b) 2(R)-(3-(Acetylthio)-2(S)-methyl-1-oxopropoxy)-3-(methylthio)propanoic acid (S)-3-(Acetylthio)-2-methylpropanoic acid (0.38 g, 2.35 mmol) and 1,1'-carbonyldiimidazole (0.38 g, 2.35 mmol) were stirred under nitrogen, in tetrahydrofuran (10 ml). After 30 min, a solution of (R)-2-hydroxy-3-(methylthio)propanoic acid (0.32 g, 2.35 mmol), triethylamine (0.33 ml, 2.35 mmol) and tetrahydrofuran (10 ml) was added dropwise. The reaction mixture was stirred at 25° for 18 h before evaporation of the solvent. The residue was acidified with dilute hydrochloric acid and extracted with ethyl acetate. The organic extracts were dried ($Na_2SO_4$) and the solvent evaporated. Chromatography on silica with dichloromethane/ethyl acetate as eluant gave the sub-title compound (0.1 g).

nmr $\delta(CDCl_3)$ 1.3 (3H, d), 2.21 (3H, s), 2.34 (3H, s), 5.32 (1H, dd);

m/z 279 ((M-1)+).

c) 2(R)-(3-Mercapto-2(S)-methyl-1-oxopropoxy)-3-(methylthio)propanoic acid 1-adamantanamine salt The product of 1b) (0.1 g, 0.357 mmol) was stirred in a solution of ammonia (1.5 ml of d. 0.88) and water (1.5 ml) for 45 min. The reaction mixture was cooled to 0° and acidified with concentrated hydrochloric acid (pH1). The solution was extracted with ethyl acetate, dried ($Na_2SO_4$) and the solvent evaporated. Chromatography on silica with dichloromethane/ethyl acetate as eluant followed by salt formation with adamantanamine gave the title salt (0.036 g), mp 205°–206°.

EXAMPLE 2

2(R)-(3-Mercapto-2(S)-methyl-1-oxopropoxy)-3-(phenylthio)propanoic acid 1-adamantanamine salt a) (R)-2-Hydroxy-3-(phenylthio)propanoic acid
Prepared by the method of Example 1a).

nmr $\delta(CDCl_3)$ 3.25 & 3.50 (2H, dd), 4.42 (1H, dd), 7.25 (3H, m), 7.46 (2H, d).

b) 2(R)-(3-(Acetylthio)-2(S)-methyl-1-oxopropoxy)-3-(phenylthio)propanoic acid
Prepared by the method of Example 1b).

nmr $\delta(CDCl_3)$ 1.25 (3H, d), 2.35 (3H, s), 5.25 (1H, dd);

m/z 414 (M+ TMS).

c) 2(R)-(3-Mercapto-2(S)-methyl-1-oxopropoxy)-3-(phenylthio)propanoic acid 1-adamantanamine salt The title salt was prepared by the method of Example 1c), mp 192°–193°.

EXAMPLE 3

α(S)-(3-Mercapto-2(S)-methyl-1-oxopropoxy)-4-nitrobenzenepropanoic acid 1-adamantanamine salt a) α(S)-(3-(Acetylthio)-2(S)-methyl-1-oxopropoxy)-4-nitrobenzenepropanoic acid Prepared by the method of Example 1b) to give the sub-title compound as a clear oil, (0.20 g, 25%).

nmr $\delta(CDCl_3)$ 8.19 (2H, d, Ph), 7.45 (2H, d, Ph), 5.33 (1H, q, CH), 3.80 (1H, br s, $CO_2H$), 3.30 (2H, m, $CH_2$), 3.05 (2H, m, $CH_2$), 2.72 (1H, m, CH), 2.30 (3H, s, $CH_3CO$), 1.24 (3H, d, $CH_3$).

b) α(S)-(3-Mercapto-2(S)-methyl-1-oxopropoxy)-4-nitrobenzenepropanoic acid 1-adamantanamine salt Prepared by the method of Example 1c) to give the title salt as a white solid (0.09 g, 39%), mp 239°–240°.

EXAMPLE 4

2(S)-(3-Mercapto-2(S)-methyl-1-oxopropoxy)-3-(phenylmethoxy)propanoic acid 1-adamantanamine salt.

a) (S)-2-Hydroxy-3-(phenylmethoxy)propanoic acid (S)-2-Amino-3-(phenylmethoxy)propanoic acid (5.0 g, 25.6 mmol) was dissolved in hydrochloric acid (26 ml of 1N) and the mixture was cooled to 0°. Sulphuric acid (39 ml of 10%) was added, the mixture cooled to 0° and a freshly prepared solution of sodium nitrite (3.90 g, 55.5 mmol) in water (30 ml) added dropwise at 0° over 2 h. The mixture was stirred at room temperature overnight, extracted with ethyl acetate, the organic extracts dried ($Na_2SO_4$) and the solvent evaporated to leave a clear oil (2.38 g). Chromatography on silica with dichloromethane/ethyl acetate as eluant gave the sub-title acid (0.78 g).

nmr $\delta(CDCl_3)$ 7.33 (5H, m, Ph), 4.61 (2H, d, $OCH_2Ph$), 4.40 (1H, t, CH), 3.82 (2H, 2xdd, $OCH_2$);

m/z 196 (M+), 91 (100%).

b) 2(S)-(3-(Acetylthio)-2(S)-methyl-1-oxopropoxy)-3-(phenylmethoxy)propanoic acid (S)-3-(Acetylthio)-2(S)-methylpropanoic acid (1.00 g, 6.12 mmol) was stirred at room temperature under nitrogen with 1,1'-carbonyldiimidazole (1.00 g, 6.12 mmol) in dry tetrahydrofuran (10 ml) for 1 h. The product of step a) (1.09 g, 5.56 mmol) and triethylamine (0.62 g, 6.12 mmol) in dry tetrahydrofuran (10 ml) was added dropwise to the pre-formed mixture. The mixture was stirred at room temperature overnight, the solvent evaporated and the residue dissolved in ethyl acetate and washed with hydrochloric acid (2N). The organic extracts were dried (Na$_2$SO$_4$) and the solvent evaporated to leave a clear oil (2.00 g). Chromatography on silica with dichloromethane/ethyl acetate (4:1) as eluant gave the sub-title compound as a clear oil (0.29 g).

nmr δ(CDCl$_3$) 7.33 (5H, m, Ph), 5.31 (1H, q, CH), 4.63 (2H, q, OCH$_2$), 3.95 (1H, dd, CH$_2$), 3.83 (1H, dd, CH$_2$), 3.10 (2H, dd, CH$_2$) 2.87 (1H, m, CH), 2.33 (3H, s, CH$_3$CO), 1.31 (3H, d, CH$_3$);

m/z 341 ((M+1)+), 91 (100%).

c) 2(S)(3-Mercapto-2(S)-methyl-1-oxopropoxy)-3-(phenylmethoxy)propanoic acid 1-adamantamine salt The product of step b) (0.28 g, 0.81 mmol), ammonia (2 ml of d. 0.88) and water (2 ml) was stirred at room temperature under nitrogen for 3 h. The mixture was then cooled in an ice/ethanol bath, acidified with hydrochloric acid (2N) and extracted with ethyl acetate. The organic extracts were dried (Na$_2$SO$_4$) and the solvent evaporated to leave a clear oil (0.18 g). HPLC on silica with dichloromethane/ethyl acetate as eluant gave a clear oil, (0.08 g, 0.264 mmol). The oil was dissolved in dry dichloromethane under nitrogen and adamantanamine (0.04 g, 0.264 mol) was added. The solvent was evaporated and trituration with diethyl ether gave the title salt as a white solid, (0.10 g, 27%), mp 205°–206°.

EXAMPLE 5

2(S)-(3-Mercapto-2(S)-methyl-1-oxopropoxy)-3-methoxypropanoic acid 1-adamantanamine salt a) (S)-2-Hydroxy-3-methoxypropanoic acid Sodium methoxide (6.60 g, 0.121 mol) was added to (R)-3-chloro-2-hydroxypropanoic acid (0.50 g, 4.0 mmol) in methanol (100 ml) and the reaction heated at reflux for 48 h. The solvent was evaporated and the residue dissolved in water/ethyl acetate. The aqueous layer was acidified with hydrochloric acid (2N) and saturated with sodium chloride. The aqueous layer was extracted with ethyl acetate (x6), the combined extracts dried (Na$_2$SO$_4$) and the solvent evaporated to give the sub-title compound (0.5 g).

nmr δ(CDCl$_3$) 4.40 (1H, t), 3.73 (2H, m), 3.40 (3H, s); m/z 264 (M+ for DiTMS).

b) (S)-2-(3-(Acetylthio)-2(S)-methyl-1-oxopropoxy)-3-methoxypropanoic acid (S)-3-(Acetylthio)-2-methylpropanoic acid (0.81 g, 5 mmol) and 1,1'-carbonyldiimidazole (0.81 g, 5 mmol) in tetrahydrofuran (20 ml) was stirred for 45 min and then a solution of the product of step a) (0.58 g, 4.85 mmol) and triethylamine (0.51 g, 5 mmol) in tetrahydrofuran (10 ml) was added dropwise. After stirring for 1 day the solvent was evaporated and the residue dissolved in ethyl acetate/hydrochloric acid (2N). The organic layer was separated, dried (Na$_2$SO$_4$) and the solvent evaporated. Reverse phase HPLC with water/methanol/trifluoroacetic acid mixtures as eluant gave the sub-title compound (0.17 g).

nmr δ(CDCl$_3$) 5.29 (1H, q), 3.43 (3H, s), 2.34 (3H, s), 1.31 (3H, d);

m/z 265 ((M+1)+).

c) 2(S)-2-(3-Mercapto-2(S)-methyl-1-oxopropoxy)-3-methoxypropanoic acid 1-adamantanamine salt The product of step b) (0.17 g, 0.64 mmol) was stirred for 3 h under nitrogen in ammonia (2 ml of d. 0.88) and water (2 ml). The mixture was cooled to 0°, acidified with hydrochloric acid (2N) and extracted with ethyl acetate (x2). The organic extract was dried (MgSO$_4$) and the solvent evaporated. HPLC on silica with dichloromethane/ethyl acetate mixtures as eluant gave the free acid (0.1 g). This was converted to the title salt with 1-adamantanamine (0.0685 g) in dichloromethane. The solvent was evaporated and the residue triturated with ether to give the title salt (0.15 g), mp 215°–216°.

EXAMPLE 6

2(S)-(3-Mercapto-2(S)-methyl-1-oxopropoxy)-4-(methylthio)butanoic acid 1-adamantanamine salt a) 2(S)-(3-(Acetylthio)-2(S)-methyl-1-oxopropoxy)-4-(methylthio)butanoic acid Prepared by the method of Example 1b) using racemic 2-hydroxy-4-(methylthio)butanoic acid and separating the diastereomers by normal phase HPLC, the required diastereomer being eluted first.

nmr δ(CDCl$_3$) 5.22 (1H, dd), 2.34 (3H, s), 2.16 (3H, s), 1.30 (3H, d);

m/z 294 (M+).

b) 2(S)-(3-Mercapto-2(S)-methyl-1-oxopropoxy)-4-(methylthio)butanoic acid 1-adamantanamine salt The title salt was prepared by the method of Example 1c), mp 222°–223°.

EXAMPLE 7

3-Ethoxy-2(S)-(3-mercapto-2(S)-methyl-1-oxopropoxy)propanoic acid 1-adamantanamine salt a) (S)-3-Ethoxy-2-hydroxypropanoic acid (R)-2-Bromo-3-hydroxypropanoic acid (2.0 g, 11.8 mmol) in ethanol (10 ml) was added to a solution of sodium (10 g, 435 mmol) in ethanol (300 ml). The mixture was heated at reflux for 48 h and the solvent evaporated. The residue was dissolved in water, acidified with hydrochloric acid and extracted with ethyl acetate. The organic extracts were dried (Na$_2$SO$_4$) and the solvent evaporated to give the title compound (0.85 g) contaminated with 2-ethoxy-3-hydroxypropanoic acid.

nmr δ(CDCl$_3$) 4.34 (1H, t), 3.73 (2H, m), 3.53 (2H, m), 1.22 (3H, m);

m/z 278 (M+ for DiTMS).

b) 2(S)-(3-(Acetylthio)-2(S)-methyl-1-oxopropoxy)-3-ethoxypropanoic acid

Prepared by the method of Example 1b) and the isomers separated by reverse phase HPLC.

m/z 350 (M+ TMS).

c) 3-Ethoxy-2(S)-(3-mercapto-2(S)-methyl-1-oxopropoxy)propanoic acid 1-adamantanamine salt The title salt was prepared by the method of Example 1c), mp 198°–199°.

EXAMPLE 8

2(S)-(3-Mercapto-2(S)-methyl-1-oxopropoxy)-3-(1-methylethoxy)propanoic acid 1-adamantanamine salt a) (S)-2-Hydroxy-3-(1-methylethoxy)propanoic acid Prepared by the method of Example 7a).
nmr δ(CDCl₃) 4.32 (1H, t), 3.80 (2H, dd);
m/z 292 (M+ for DiTMS).

b) 2(S)-(3-(Acetylthio)-2(S)-methyl-1-oxopropoxy)-3-(1-methylethoxy)propanoic acid Prepared by the method of Example 1b).
nmr δ(CDCl₃) 5.29 (1H, dd), 2.34 (3H, s), 1.33 (3H, d), 1.19 (6H, 2xd).

c) 2(S)-(3-Mercapto-2(S)-methyl-1-oxopropoxy)-3-(1-methylethoxy)propanoic acid 1-adamantanamine salt The title salt was prepared by the method of Example 1c), mp 212°–213°.

EXAMPLE 9

2(S)-(3-Mercapto-2(S)-methyl-1-oxopropoxy)-3-phenoxypropanoic acid 1-adamantanamine salt a) (S)-2-Hydroxy-3-phenoxypropanoic acid Platinum oxide (1.0 g) in acetic acid (20 ml) was hydrogenated at 1 atmosphere for 1.5 h. The platinum was filtered off, washed with water and added to a solution of (R)-3-phenoxy-1,2-propanediol (1.0 g, 6 mmol) and sodium bicarbonate (0.5 g) in water (120 ml). Air was blown through the vigorously stirred mixture overnight. The mixture was filtered, the aqueous solution acidified with hydrochloric acid and extracted with ethyl acetate. The organic extracts were dried (Na₂SO₄) and the solvent evaporated to give the sub-title acid (0.9 g).
nmr δ(CDCl₃) 4.20 (1H, m), 4.00 (2H, m);
m/z 326 (M+ for DiTMS).

b) 2(S)-(3-(Acetylthio)-2(S)-methyl-1-oxopropoxy)-3-phenoxypropanoic acid

Prepared by the method of Example 1b).
nmr δ(CDCl₃) 7.30 (2H, t), 6.95 (1H, t), 6.92 (2H, d), 5.50 (1H, dd), 2.32 (3H, s), 1.30 (3H, d);
m/z 398 (M+ TMS).

c) 2(S)-(3-Mercapto-2(S)-methyl-1-oxopropoxy)-3-phenoxypropanoic acid 1-adamantanamine salt The title salt was prepared by the method of Example 1c), mp 195°–196°.

EXAMPLE 10

3-(1,1-Dimethylethoxy)-2(S)-(3-mercapto-2(S)-methyl-1-oxopropoxy)propanoic acid 1-adamantanamine salt a) (S)-3-(1,1-Dimethylethoxy)-2-hydroxypropanoic acid Prepared by the method of Example 4a).
nmr δ(CDCl₃) 4.28 (1H,t), 1.23 (9H, s).

b) 2(S)-(3-(Acetylthio)-2(S)-methyl-1-oxopropoxy)-3-(1,1-dimethylethoxy)propanoic acid Prepared by the method of Example 1b).
nmr δ(CDCl₃) 5.24 (1H, dd), 2.34 (3H, s), 1.32 (3H, d), 1.20 (9H, s).

c) 3-(1,1-Dimethylethoxy)-2(S)-(3-mercapto-2(S)-methyl-1-oxopropoxy)propanoic acid 1-adamantanamine salt The title salt was prepared by the method of Example 1c), mp 247°–248°.

EXAMPLE 11

2(R)-(3-Mercapto-2(S)-methyl-1-oxopropoxy)-3-(phenylsulphonyl)propanoic acid 1-adamantanamine salt a) (R)-2-Hydroxy-3-(phenylsulphonyl)propanoic acid (R)-2-Hydroxy-3-(phenylthio)propanoic acid (0.27 g, 1.4 mmol) was added to a stirred solution of oxone (1.25 g, 4.2 mmol) in water (5 ml). The solution was stirred for 30 min then extracted with ethyl acetate. The organic extracts were dried and the solvent evaporated to give the sub-title compound (0.3 g).
nmr δ(CDCl₃) 7.80 (5H, m), 4.72 (1H, dd), 3.73 (1H, dd).

b) 2(R)-(3-(Acetylthio)-2(S)-methyl-1-oxopropoxy)-3-(phenylsulphonyl)propanoic acid Prepared by the method of Example 1b).
nmr δ(CDCl₃) 5.56 (1H, t), 3.74 (2H, d), 2.34 (3H, s), 1.16 (3H, d);
m/z 375 ((M+1)+).

c) 2(R)-(3-Mercapto-2(S)-methyl-1-oxopropoxy)-3-(phenylsulphonyl)propanoic acid 1-adamantanamine salt The title salt was prepared by the method of Example 1c), mp 184°–185°.

EXAMPLE 12

3-(Ethylthio)-2(R)-(3-mercapto-2(S)-methyl-1-oxopropoxy)propanoic acid 1-adamantanamine salt a) (R)-3-(Ethylthio)-2-hydroxypropanoic acid Sodium (0.57 g, 25 mmol) in ethanol (25 ml) was added dropwise to a stirred solution of (R)-2-bromo-3-hydroxypropanoic acid (2.11 g, 12.5 mmol) under nitrogen at −30°. After 30 min the mixture was allowed to warm to room temperature and stirred for a further 1 h. A solution of ethanethiol (1.85 ml, 25 mmol) in sodium ethoxide/ethanol (0.57 g, 25 mmol of sodium in 25 ml ethanol) was added and the mixture stirred overnight. The ethanol was evaporated and the residue dissolved in water. The solution was acidified with hydrochloric acid and extracted with ethyl acetate, the organic extracts were dried (MgSO₄) and the solvent evaporated. Chromatography on silica with toluene/acetic acid as eluant gave the sub-title acid (0.79 g).
nmr δ(CDCl₃) 4.10 (1H, m), 2.55 (2H, q), 1.16 (3H, t);
m/z 294 (M+ for DiTMS).

b) (R)-3-(Ethylthio)-2-hydroxypropanoic acid 2-propenyl ester

Chlorotrimethylsilane (1.9 ml, 15 mmol) was added to a stirred solution of the product of step a) (0.75 g, 5 mmol) in 2-propen-1-ol (5 ml). After 2 h the solvent was evaporated to give the sub-title ester (0.95 g).
nmr δ(CDCl₃) 4.70 (2H, d), 2.62 (2H, q), 1.27 (3H, t);
m/z 262 (M+ for TMS).

c) 2(R)-(3-(Acetylthio)-2(S)-methyl-1-oxopropoxy)-3-(ethylthio)propanoic acid 2-propenyl ester Dicyclohexylcarbodiimide (1.13 g, 5.5 mmol) in dichloromethane (20 ml) was added to a stirred solution of the product of step b) (0.95 g, 5 mmol), (S)-3-(Acetylthio)-2-methylpropanoic acid (0.81 g, 5 mmol) and 4-(dimethylamino)pyridine (0.06 g, 0.5 mmol) in dichloromethane (30 ml). The mixture was stirred overnight, filtered and the solvent evaporated. The residue was dissolved in ethyl acetate, filtered and washed with potassium hydrogen sulphate solution, sodium bicarbonate solution and brine and the solvent evaporated. Chromatography on silica with ethyl acetate/petroleum ether as eluant gave the sub-title compound (1.1 g).
nmr δ(CDCl₃) 4.66 (2H, d), 2.63 (2H, q), 2.33 (3H, s), 1.30 (2×3H, t and d).

d) 2(R)-(3-(Acetylthio)-2(S)-methyl-1-oxopropoxy)-3-(ethylthio)propanoic acid

The product of step c) (1.05 g, 3.1 mmol) and tris-(triphenylphosphine)rhodiumIchloride (325 mg added over 6 days) in ethanol (10 ml) containing water (2 drops) were heated at reflux for 6 days. The solvent was evaporated and chromatography on silica with toluene/acetic acid as eluant gave the sub-title compound (0.43 g).

nmr δ(CDCl$_3$) 5.08 (1H, dd), 2.6 (2H, q), 2.3 (3H, s), 1.18 (2×3H, t and d);

m/z 366 (M+ for TMS).

e) 3-(Ethylthio)-2(R)-(3-mercapto-2(S)-methyl-1-oxopropoxy)propanoic acid 1-adamantanamine salt The title salt was prepared by the method of Example 1c), mp 207°–208°.

EXAMPLE 13

2(S)-(3-Mercapto-2(S)-methyl-1-oxopropoxy)butanedioic acid 4-methyl ester 1-adamantanamine salt a) (S)-2-Hydroxybutanedioic acid 1-(2-propenyl)ester Trifluroacetic anhydride (74.35 g, 0.35 mol) was added to (S)-2-hydroxybutanedioic acid (20 g, 0.149 mol) at 0°. After 2¼ h the solvent was evaporated at 0° and 2-propen-1-ol (100 ml) added at 0°. The mixture was allowed to warm to room temperature and stirred for a further 3½ h. The solvent was evaporated and chromatography on silica with dichloromethane/ethyl acetate as eluant gave the sub-title ester (10.93 g).

nmr δ(CDCl$_3$) 4.71 (2H, d), 4.50 (1H, d).

b) (S)-2-Hydroxybutanedioic acid 4-methyl 1-(2-propenyl) ester

Iodomethane (0.9 g, 6.3 mmol) was added to a stirred mixture of the product of step a) (1.0 g, 5.7 mmol) and potassium carbonate (0.87 g, 6.3 mmol) in dimethylformamide (10 ml). After 3 h, water and ethyl acetate were added and the aqueous layer extracted with ethyl acetate. The organic extracts were washed with brine, dried (Na$_2$SO$_4$) and the solvent evaporated to give the sub-title diester (0.7 g).

nmr δ(CDCl$_3$) 4.71 (2H, d), 3.72 (3H, s).

c) 2(S)-(3-(Acetylthio)-2(S)-methyl-1-oxopropoxy)-butanedioic acid 4-methyl 1-(2-propenyl) ester Prepared by the method of Example 12c).

nmr δ(CDCl$_3$) 4.65 (2H, d), 3.73 (3H, s), 2.33 (3H, s), 1.30 (3H, d);

m/z 332 (M+).

d) 2(S)-(3-(Acetylthio)-2(S)-methyl-1-oxopropoxy)-butanedioic acid 4-methyl ester Prepared by the method of Example 15d).

nmr δ(CDCl$_3$) 3.75 (3H, s), 2.36 (3H, s), 1.29 (3H, d); m/z 364 (M+ for TMS).

e) 2(S)-(3-Mercapto-2(S)-methyl-1-oxopropoxy)-butanedioic acid 4-methyl ester 1-adamantanamine salt 2-Aminoethanethiol (0.146 g, 1.9 mmol) was added to a stirred solution of the product of step d) (0.25 g, 0.87 mmol) in acetonitrile (4 ml) under nitrogen. After 2 h the solvent was evaporated and the residue dissolved in ethyl acetate/hydrochloric acid. The organic layer was dried (Na$_2$SO$_4$) and the solvent evaporated. HPLC on silica with dichloromethane/ethyl acetate as eluant gave the title compound as the free acid (0.09 g). This was converted to the 1-adamantanamine salt which was triturated with ether to give the title compound as a colourless solid (0.14 g), mp 197°–198°.

EXAMPLE 14

2(R)-(3-Mercapto-2(S)-methyl-1-oxopropoxy)-3-((phenylmethyl)thio)propanoic acid 1-adamantanamine salt a) (R)-2-Hydroxy-3-((phenylmethyl)thio)propanoic acid Prepared by the method of Example 12a).

nmr δ(CDCl$_3$) 3.78 (2H, s), 2.70 and 2.60 (2×1H, 2×dd);

m/z 356 (M+ for DiTMS).

b) 2(R)-(3-(Acetylthio)-2(S)-methyl-1-oxopropoxy)-3-((phenylmethyl)thio)propanoic acid Prepared by the method of Example 1b).

nmr δ(CDCl$_3$) 5.25 (1H, q), 3.80 (2H, s), 2.33 (3H, s), 1.32 (3H, d);

m/z 441 ((M+Rb)+).

c) 2(R)-(3-Mercapto-2(S)-methyl-1-oxopropoxy)-3-((phenylmethyl)thio)propanoic acid 1-adamantanamine salt The title salt was prepared by the method of Example 1c), mp 176°–177°.

EXAMPLE 15

2(S)-(3-Mercapto-2(S)-methyl-1-oxopropoxy)-3-((methylsulphonyl)amino)propanoic acid 1-adamantanamine salt a) (S)-3-Amino-2-hydroxypropanoic acid 2-propenyl ester Prepared by the method of Example 12b).

nmr δ(DMSO) 4.58 (2H, d) 4.36 (1H, q);

m/z 219 ((M+1)+ for TMS).

b) (S)-2-Hydroxy-3-((methylsulphonyl)amino)-propanoic acid 2-propenyl ester

Methanesulphonyl chloride (0.74 ml, 8.8 mmol) in acetonitrile (30 ml) was added to a stirred solution of the product of step a) (1.6 g, 8.8 mmol) and triethylamine (2.5 ml, 17.6 mmol) in acetonitrile (30 ml) at 0°. After stirring overnight the solvent was evaporated and the residue dissolved in ethyl acetate/water. The organic extract was dried (MgSO$_4$) and the solvent evaporated to give the sub-title compound (1.55 g).

nmr δ(CDCl$_3$) 4.72 (2H, d), 4.37 (1H, q), 2.99 (3H, s); m/z 367 (M+ for DiTMS).

c) 2(S)-(3-(Acetylthio)-2(S)-methyl-1-oxopropoxy)-3-((methylsulphonyl)amino)propanoic acid 2-propenyl ester Prepared by the method of Example 12c).

nmr δ(CDCl$_3$) 4.67 (2H, d), 3.00 (3H, s), 2.36 (3H, s), 1.30 (3H, d);

m/z 368 ((M+1)+).

d) 2(S)-(3-(Acetylthio)-2(S)-methyl-1-oxopropoxy)-3-((methylsulphonyl)amino)propanoic acid Morpholine (0.42 ml, 4.9 mmol) was added to a stirred solution at 0° of the product of step c) (1.8 g, 4.9 mmol) and tetrakis(triphenylphosphine)palladium (0) (0.23 g) in tetrahydrofuran (50 ml). After stirring at room temperature for 4 h ethyl acetate/hydrochloric acid were added. The organic layer was dried (MgSO$_4$) and the solvent evaporated. Chromatography gave the sub-title compound as a colourless oil (1.08 g).

nmr δ(CDCl$_3$) 3.03 (3H, s), 2.35 (3H, s), 1.30 (3H, d); m/z 328 ((M+1)+).

e) 2(S)-(3-Mercapto-2(S)-methyl-1-oxopropoxy)-3-((methylsulphonyl)amino)propanoic acid 1-adamantanamine salt The title salt was prepared by the method of Example 1c), mp 202°–203°.

EXAMPLE 16

2(R)-(3-Mercapto-2(S)-methyl-1-oxopropoxy)-3-((1-methylethyl)thio)propanoic acid 1-adamantanamine salt a) (R)-2-Hydroxy-3-((1-methylethyl)thio)propanoic acid Sodium (7.09 g, 308 mmol) in methanol (100 ml) was added over 35 min to a stirred solution of (R)-2-bromo-3-hydroxypropanoic acid (25.5 g, 151 mmol) in methanol (200 ml) at −25°. The temperature was allowed to reach 10° and the mixture stirred for a further 2 h. 2-Propanethiol (11.4 ml, 240 mmol) in sodium methoxide solution, prepared from sodium (5.68 g, 247 mmol) and methanol (100 ml) was added to this suspension (240 ml, 120 mmol) at −5°. After 16 h at room temperature the solvent was evaporated and the residue dissolved in water/ether/conc. hydrochloric acid to a final pH of approximately 1. The organic phase was separated and the aqueous phase re-extracted with ether (×2). The combined organic extracts were dried ($Na_2SO_4$) and the solvent evaporated to give the sub-title compound (18.56 g).

nmr δ($CDCl_3$) 4.44 (1H, dd), 1.28 (6H, d);
m/z 308 ($M^+$ for DiTMS).

b) 2(R)-(3-(Acetylthio)-2(S)-methyl-1-oxopropoxy)-3-((1-methylethyl)thio)propanoic acid Carbonyl diimidazole (2.23 g, 13.8 mmol) was added to a stirred solution of (S)-3-(acetylthio)-2-methylpropanoic acid (2.23 g, 13.8 mmol) in tetrahydrofuran (30 ml). After 40 min a solution of the product of step a) (2.23 g, 13.8 mmol) and triethylamine (1.95 ml, 13.8 mmol) in tetrahydrofuran (10 ml) was added. After stirring for 5 days the solvent was evaporated and the residue dissolved in ethyl acetate/hydrochloric acid (2N). The organic layer was separated, dried ($Na_2SO_4$) and the solvent evaporated to give the sub-title compound (3.6 g).

nmr δ($CDCl_3$) 5.26 (1H, dd), 1.32 (3H, d), 1.31 (6H, d);
m/z 393 ((M+Rb)$^+$).

c) 2(R)-(3-Mercapto-2(S)-methyl-1-oxopropoxy)-3-((1-methylethyl)thio)propanoic acid 1-adamantanamine salt Aqueous ammonia (5 ml of d. 0.88 and 10 ml water) was added to the product of step b) (1.14 g) at 0°. After 1.75 h the reaction was acidified to pH 1 with concentrated hydrochloric acid. The aqueous solution was extracted with ethyl acetate and the organic extract dried ($Na_2SO_4$). Evaporation of the solvent followed by chromatography on silica with toluene/acetic acid mixtures as eluant gave the sub-title compound as the free acid (0.2 g), which was converted to the 1-adamantanamine salt, mp 218°–219°.

EXAMPLE 17

3-(Acetylamino)-2(S)-(3-mercapto-2(S)-methyl-1-oxopropoxy)propanoic acid 1-adamantanamine salt a) (S)-3-(Acetylamino)-2-hydroxypropanoic acid 2-propenyl ester Prepared by the method of Example 15b).
nmr δ($CDCl_3$) 4.66 (2H, m), 1.99 (3H, s).

b) 3-(Acetylamino)-2(S)-(3-(acetylthio)-2(S)-methyl-1-oxopropoxy)propanoic acid 2-propenyl ester Prepared by the method of Example 12c).
nmr δ($CDCl_3$) 4.64 (2H, d), 2.35 (3H, s), 2.05 (3H, s), 1.26 (3H, d);
m/z 322 ((M+1)$^+$).

c) 3-(Acetylamino)-2(S)-(3-(acetylthio)-2(S)-methyl-1-oxopropoxy)propanoic acid

Prepared by the method of Example 15d).
nmr δ($CDCl_3$) 2.35 (3H, s), 2.07 (3H, s), 1.28 (3H, d);
m/z 332 ((M+1)$^+$).

d) 3-(Acetylamino)-2(S)-(3-mercapto-2(S)-methyl-1-oxopropoxy)propanoic acid 1-adamantanamine salt The title salt was prepared by the method of Example 1c), mp 192°–193°.

EXAMPLE 18

4-Amino-2(S)-(3-mercapto-2(S)-methyl-1-oxopropoxy)-4-oxobutanoic acid 1-adamantanamine salt a) (S)-4-Amino-2-hydroxy-4-oxobutanoic acid 2-propenyl ester Prepared by the method of Example 12b).
nmr δ($CDCl_3$) 5.90 (1H, m), 5.35 (2H, m), 2.80 (2H, m);
m/z 174 ((M+1)$^+$).

b) 2(S)-(3-(Acetylthio)-2(S)-methyl-1-oxopropoxy)-4-amino-4-oxobutanoic acid 2-propenyl ester Prepared by the method of Example 12c).
nmr δ($CDCl_3$) 4.67 (2H, dd), 2.34 (3H, s), 1.28 (3H, d);
m/z 318 ((M+1)$^+$).

c) 2(S)-(3-(Acetylthio)-2(S)-methyl-1-oxopropoxy)-4-amino-4-oxobutanoic acid

Prepared by the method of Example 15d).
nmr δ($CDCl_3$) 4.67 (2H, dd), 2.34 (3H, s), 1.28 (3H, d);
m/z 278 ((M+1)$^+$).

d) 4-Amino-2(S)-(3-mercapto-2(S)-methyl-1-oxopropoxy)-4-oxobutanoic acid 1-adamantanamine salt The title salt was prepared by the method of Example 1c), mp 177°–178°.

EXAMPLE 19

3-((1.1-Dimethylethyl)thio)-2(R)-(3-mercapto-2(S)-methyl-1-oxopropoxy)propanoic acid 1-adamantanamine salt a) (R)-3-((1,1-Dimethylethyl)thio)-2-hydroxypropanoic acid Prepared by the method of Example 12a).
nmr δ($CDCl_3$) 4.45 (1H, dd), 1.34 (9H, s);
m/z 179 ((M+1)$^+$).

b) 2(R)-(3-(Acetylthio)-2(S)-methyl-1-oxopropoxy-3-((1-dimethylethyl)thio)propanoic acid Prepared by the method of Example 1b).
nmr δ($CDCl_3$) 5.25 (1H, dd), 2.34 (3H, s), 1.34 (9H, s), 1.30 (3H, d);
m/z 407 ((M+Rb)$^+$).

c) 3-((1,1-Dimethylethyl)thio)-2(R)-(3-mercapto-2(S)-methyl-1-oxopropoxy)propanoic acid 1-adamantanamine salt The title salt was prepared by the method of Example 1c), mp 232°–233°.

EXAMPLE 20

3-Chloro-2(R)-(3-mercapto-2(S)-methyl-1-oxopropoxy)propanoic acid 1-adamantanamine salt a) 2(R)-(3-(Acetylthio)-2(S)-methyl-1-oxopropoxy)-3-chloropropanoic acid Prepared by the method of Example 1b).
nmr δ($CDCl_3$) 5.45 (1H, dd), 2.34 (3H, s), 1.33 (3H, d);
m/z 269 ((M+1)$^+$).

b) 3-Chloro-2(R)-(3-mercapto-2(S)-methyl-1-oxopropoxy)propanoic acid 1-adamantanamine salt The title salt was prepared by the method of Example 13e), mp 190°–190.5°.

EXAMPLE 21

α(S)-(2(S)-(Mercaptomethyl)-3-phenyl-1-oxopropoxy)-benzenepropanoic acid 1-adamantanamine salt a) α(S)-(2(S)-((Acetylthio)methyl)-3-phenyl-1-oxopropoxy)benzenepropanoic acid Prepared by the method of Example 1b) using racemic 2-((acetylthio)methyl)benzenepropanoic acid and separating the diastereomers by HPLC.

nmr δ(CDCl$_3$) 5.20 (1H, m), 2.24 (3H, s);
m/z 458 (M+ for TMS).

b) α(S)-(2(S)-(Mercaptomethyl)-3-phenyl-1-oxopropoxy)benzenepropanoic acid 1-adamantanamine salt The title salt was prepared by the method of Example 1c), mp 167°.

EXAMPLE 22

α(S)-(2(S)-(Mercaptomethyl)-4-(4-methoxyphenyl)-1-oxobutoxy)benzenepropanoic acid 1-adamantanamine salt a) α(S)-(2-((Acetylthio)methyl)-4-(4-methoxyphenyl)-1-oxobutoxy)benzenepropanoic acid 2-propenyl ester Prepared by the method of Example 12c) using racemic α-((acetylthio)methyl)-4-methoxybenzenebutanoic acid and isolating the diastereomeric mixture.

nmr δ(CDCl$_3$) 3.80 (3H, 2xs), 2.30 (3H, 2xs);
m/z 470 (M+).

b) α(S)-(2(S)-((Acetylthio)methyl)-4-(4-methoxyphenyl)-1-oxobutoxy)benzenepropanoic acid Prepared by the method of Example 15d) and separating the diastereomers by chromatography on silica.

nmr δ(CDCl$_3$) 5.30 (1H, m), 3.80 (3H, s), 2.30 (3H, s);
m/z 430 (M+).

c) α(S)-(2(S)-(Mercaptomethyl)-4-(4-methoxyphenyl)-1-oxobutoxy)benzenepropanoic acid 1-adamantanamine salt The title salt was prepared by the method of Example 1c), mp 169°-170°.

EXAMPLE 23

α(S)-(3-Mercapto-2-(mercaptomethyl)-1-oxopropoxy)-benzenepropanoic acid 1-adamantanamine salt a) α(S)-(3-(Acetylthio)-2-((acetylthio)methyl)-1-oxopropoxy)benzenepropanoic acid Prepared by the method of Example 1b).

nmr δ(CDCl$_3$) 5.30 (1H, dd), 2.32 (3H, s), 2.31 (3H, s);
m/z 456 (M+ for TMS).

b) α(S)-(3-Mercapto-2-(mercaptomethyl)-1-oxopropoxy)benzenepropanoic acid 1-adamantanamine salt The title salt was prepared by the method of Example 1c), mp 198°-199°.

EXAMPLE 24

α(S)-(3-Mercapto-2(S)-methyl-1-oxopropoxy)-1,3-dithiolane-2-propanoic acid 1-adamantanamine salt a) α(S)-Acetoxy-1,3-dithiolane-2-propanoic acid ethyl ester Boron trifluoride etherate (1.15 g, 81 mmol) was added to a stirred solution of 1,2-ethanedithiol (0.34 g, 3.65 mmol) and (S)-2-acetoxy-4-oxobutanoic acid ethyl ester (0.46 g, 2.4 mmol) in dichloromethane (20 ml) at 0°. The mixture was stirred at room temperature overnight and ice/water added. The organic layer was separated, dried (MgSO$_4$) and the solvent evaporated to give the sub-title compound (0.92 g).

nmr δ(CDCl$_3$) 4.22 (2H, q), 2.30 (2H, m), 2.18 (3H, s), 1.28 (3H, t);
m/z 219 ((M-OEt)+).

b) α(S)-Hydroxy-1,3-dithiolane-2-propanoic acid

Potassium hydroxide (11.5 ml of 1N in water) was added to the product of step a) (0.92 g, 3.5 mmol) in tetrahydrofuran (12 ml). After 4 h the reaction mixture was acidified with hydrochloric acid (2N) and extracted with ethyl acetate. The organic extract was dried (MgSO$_4$) and the solvent evaporated to give the sub-title acid (0.47 g).

nmr δ(CDCl$_3$) 4.77 (1H, q), 4.40 (1H, dd), 3.28 (4H, m);
m/z 323 (M+ for DiTMS).

c) α(S)-(3-(Acetylthio)-2(S)-methyl-1-oxopropoxy)-1,3-dithiolane-2-propanoic acid Prepared by the method of Example 1b).

nmr δ(CDCl$_3$) 5.22 (1H, q), 4.60 (1H, q), 2.34 (3H, s), 1.30 (3H, d).

d) α(S)-(3-Mercapto-2(S)-methyl-1-oxopropoxy)-1,3-dithiolane-2-propanoic acid 1-adamantanamine salt The title salt was prepared by the method of Example 1c), mp 223°-224°.

EXAMPLE 25

2(R)-(3-Mercapto-2(S)-methyl-1-oxopropoxy)-3-(1-naphthalenylthio)propanoic acid 1-adamantanamine salt a) (R)-2-Hydroxy-3-(1-naphthalenylthio)propanoic acid Prepared by the method of Example 12a).

nmr δ(CDCl$_3$) 4.20 (1H, dd), 3.28 (1H, dd);
m/z 392 (M+ for DiTMS).

b) 2(R)-(3-(Acetylthio)-2(S)-methyl-1-oxopropoxy)-3-(1-naphthalenylthio)propanoic acid Prepared by the method of Example 1b).

nmr δ(CDCl$_3$) 5.22 (1H, q), 2.90 (2H, dd), 2.32 (3H, s), 1.18 (3H, d);
m/z 464 (M+ for TMS).

c) 2(R)-(3-Mercapto-2(S)-methyl-1-oxopropoxy)-3-(1-naphthalenylthio)propanoic acid 1-adamantanamine salt The title salt was prepared by the method of Example 1c), mp 199°-200°.

EXAMPLE 26

α(S)-(3-Mercapto-2(S)-methyl-1-oxopropoxy)cyclohexane-propanoic acid 1-adamantanamine salt a) α(S)-Hydroxycyclohexanepropanoic acid α(S)-Hydroxybenzene propanoic acid (4.99 g, 30 mmol) was hydrogenated at 4 bar in ethanol (175 ml) and acetic acid (10 ml) using platinum oxide (0.5 g) as catalyst. After filtration, evaporation of the solvent gave the sub-title acid (4.92 g).

nmr δ(CDCl$_3$) 4.33 (1H, dd);
m/z 316 (M+ for DiTMS).

b) α(S)-(3-(Acetylthio)-2(S)-methyl-1-oxopropoxy)cyclohexanepropanoic acid

Prepared by the method of Example 1b).

nmr δ(CDCl$_3$) 5.10 (1H, dd), 2.34 (3H, s);
m/z 388 (M+ for TMS).

c) α(S)-(3-Mercapto-2(S)-methyl-1-oxopropoxy)cyclohexanepropanoic acid 1-adamantanamine salt The title salt was prepared by the method of Example 1c), mp 230°-232°.

EXAMPLE 27

3-Cyano-2(S)-(3-mercapto-2(S)-methyl-1-oxopropoxy)-propanoic acid 1-adamantanamine salt a) 2(S)-(3-(Acetylthio)-2(S)-methyl-1-oxopropoxy)-3-cyanopropanoic acid 2-propenyl ester Trichloroacetyl chloride (0.3 g, 1.7 mmol) in dichloromethane (20 ml) was added at 0°–5° to a stirred solution of 2(S)-(3-(acetylthio)-2(S)-methyl-1-oxopropoxy)-4-amino-4-oxobutanoic acid 2-propenyl ester (0.48 g, 1.5 mmol) and triethylamine (0.31 g, 3 mmol) in dichloromethane (50 ml). The mixture was stirred overnight, the organic solution washed with water, dried (MgSO$_4$) and the solvent evaporated to give the sub-title ester (0.49 g).

nmr δ(CDCl$_3$) 4.69 (2H, dd), 2.35 (3H, s), 1.33 (3H, d);

m/z 299 (M+).

b) 2(S)-(3-(Acetylthio)-2(S)-methyl-1-oxopropoxy)-3-cyanopropanoic acid

Prepared by the method of Example 15d).

nmr δ(CDCl$_3$) 5.38 (1H, t), 3.18 (2H, dd), 3.00 (2H, d), 2.35 (3H, s) 1.29 (3H, d).

c) 3-Cyano-2(S)-(3-mercapto-2(S)-methyl-1-oxopropoxy)propanoic acid 1-adamantanamine salt The title salt was prepared by the method of Example 1c), mp 194°–195°.

EXAMPLE 28

2(S)-(3-Mercapto-1-oxopropoxy)-3-(phenylmethoxy)propanoic acid 1-adamantanamine salt a) 2(S)-(3-(Acetylthio)-1-oxopropoxy)-3-(phenylmethoxy)propanoic acid 3-(Acetylthio)propanoyl chloride (0.26 g, 1.56 mmol) and (S)-2-hydroxy-3-(phenylmethoxy)propanoic acid (0.3 g, 1.53 mmol) were heated at 60° for 1 h. The cooled reaction mixture was purified by chromatography on silica with dichloromethane/acetic acid mixtures as eluant to give the sub-title acid (0.25 g).

m/z 326 (M+).

b) 2(S)-(3-Mercapto-1-oxopropoxy)-3-(phenylmethoxy)propanoic acid 1-adamantanamine salt The title salt was prepared by the method of Example 13e), mp 179°–180°.

EXAMPLE 29

2(S)-(3-Mercapto-2(S)-methyl-1-oxopropoxy)-3-((phenylsulphonyl)amino)propanoic acid 1-adamantanamine salt a) (S)-2-Hydroxy-3-((phenylsulphonyl)amino)propanoic acid 2-propenyl ester Prepared by the method of Example 15b).

nmr δ(CDCl$_3$) 5.85 (1H, m), 5.00 (1H, t), 4.30 (1H, t); m/z 286 ((M+1)+).

b) 2(S)-(3-(Acetylthio)-2(S)-methyl-1-oxopropoxy)-3-((phenylsulphonyl)amino)propanoic acid Prepared by the method of Example 12c).

nmr δ(CDCl$_3$) 5.14 (1H, t), 5.08 (1H, q), 2.35 (3H, s), 1.22 (3H, d);

m/z 430 ((M+1)+).

c) 2(S)-(3-(Acetylthio)-2(S)-methyl-1-oxopropoxy)-3-((phenylsulphonyl)amino)propanoic acid Prepared by the method of Example 15d).

nmr δ(CDCl$_3$) 5.12 (1H, t), 3.49 (1H, t), 1.25 (3H, d); m/z 390 ((M+1)+).

d) 2(S)-(3-Mercapto-2(S)-methyl-1-oxopropoxy)-3-((phenylsulphonyl)amino)propanoic acid 1-adamantanamine salt The title salt was prepared by the method of Example 1c), mp 195°–196°.

EXAMPLE 30

2(R)-(3-Mercapto-2(S)-methyl-1-oxopropoxy)-3-(2-thienylthio)propanoic acid 1-adamantanamine salt a) (R)-2-Hydroxy-3-(2-thienylthio)propanoic acid Prepared by the method of Example 1a).

nmr δ(CDCl$_3$) 4.40 (1H, dd), 3.28 (1H, dd), 3.10 (1H, dd);

m/z 348 (M+ for DiTMS).

b) 2(R)-(3-(Acetylthio)-2(S)-methyl-1-oxopropoxy)-3-(2-thienylthio)propanoic acid Prepared by the method of Example 28a).

nmr δ(CDCl$_3$) 7.40 (1H, dd), 7.19 (1H, dd), 6.99 (1H, dd), 5.22 (1H, dd), 2.34 (3H, s), 1.27 (3H, d);

m/z 348 (M+).

c) 2(R)-(3-Mercapto-2(S)-methyl-1-oxopropoxy)-3-(2-thienylthio)propanoic acid 1-adamantanamine salt The title salt was prepared by the method of Example 1c), mp 192°–193°.

EXAMPLE 31

2(S)-(3-Mercapto-2(S)-methyl-1-oxopropoxy)-3-(methyl(methylsulphonyl)amino)propanoic acid 1-adamantanamine salt a) (S)-2-Hydroxy-3-(methyl(methylsulphonyl)amino)propanoic acid 2-propenyl ester (S)-2-Hydroxy-3-((methylsulphonyl)amino)propanoic acid 2-propenyl ester (0.9 g, 4.04 mmol), iodomethane (9 ml) and potassium carbonate (0.64 g) in acetone (50 ml) were heated at reflux for 20 h. The solvent was evaporated and the residue dissolved in water/ethyl acetate. The organic layer was separated, dried (MgSO$_4$) and the solvent evaporated to give the sub-title ester (0.83 g).

nmr δ(CDCl$_3$) 4.71 (2H, t), 2.99 (3H, s), 2.89 (3H, s); m/z 238 ((M+1)+).

b) 2(S)-(3-(Acetylthio)-2(S)-methyl-1-oxopropoxy)-3-(methyl(methylsulphonyl)amino)propanoic acid 2-propenyl ester Prepared by the method of Example 12c).

nmr δ(CDCl$_3$) 4.66 (2H, d), 2.99 (3H, s), 2.86 (3H, s), 2.33 (3H, s), 1.27 (3H, d);

m/z 382 ((M+1)+).

c) 2(S)-(3-(Acetylthio)-2(S)-methyl-1-oxopropoxy)-3-(methyl(methylsulphonyl)amino)propanoic acid Prepared by the method of Example 15d).

nmr δ(CDCl$_3$) 5.30 (1H, q), 2.99 (3H, s), 2.89 (3H, s), 2.34 (3H, s), 1.32 (3H, d);

m/z 392 (M+ for TMS).

d) 2(S)-(3-Mercapto-2(S)-methyl-1-oxopropoxy)-3-(methyl(methylsulphonyl)amino)propanoic acid 1-adamantanamine salt The title salt was prepared by the method of Example 1c), mp 204°–205°.

EXAMPLE 32

2(S)-(3-Mercapto-2(S)-methyl-1-oxopropoxy)-4-phenoxybutanoic acid 1-adamantanamine salt a) (S)-2-Acetoxy-4-phenoxybutanoic acid ethyl ester Diethyl azodicarboxylate (1.37 g, 7.9 mmol) in tetrahydrofuran (3 ml) was added to a stirred mixture of (S)-2-acetoxy-4-hydroxybutanoic acid ethyl ester (1.0 g, 5.3 mmol), phenol (0.74 g, 7.9 mmol) and triphenylphosphine (2.07 g, 7.9 mmol) in tetrahydrofuran (16 ml). After 4 days the solvent was evaporated and the residue purified by chromatography on silica with ethyl acetate/petroleum ether (60°–80°) mixtures as eluant, to give the sub-title compound (1.4 g).

nmr δ(CDCl$_3$) 7.28 (2H, dd), 5.23 (1H, dd), 4.24 (2H, q), 2.10 (3H, s), 1.27 (3H, t);

m/z 266 (M+).

b) (S)-2-Hydroxy-4-phenoxybutanoic acid

Prepared by the method of Example 24b).

nmr δ(CDCl$_3$) 7.29 (2H, m), 6.96 (3H, m), 4.54 (1H, dd), 4.21 (2H, t);

m/z 340 (M+ for DiTMS).

c) 2(S)-(3-(Acetylthio)-2(S)-methyl-1-oxopropoxy)-4-phenoxybutanoic acid

Prepared by the method of Example 28a).

nmr δ(CDCl$_3$) 7.28 (2H, d), 5.35 (1H, q), 3.08 (2H, d), 2.25 (3H, s), 1.28 (3H, d);

m/z 412 (M+ for TMS).

d) 2(S)-(3-Mercapto-2(S)-methyl-1-oxopropoxy)-4-phenoxybutanoic acid 1-adamantanamine salt The title salt was prepared by the method of Example 1c), mp 189°–190°.

EXAMPLE 33

2(S)-(3-Mercapto-2(S)-methyl-1-oxopropoxy)-4-((1-methylethyl)thio)butanoic acid 1-adamantanamine salt a) (S)-2-Acetoxy-4-(((4-methylphenyl)sulphonyl)oxy)-butanoic acid ethyl ester (S)-2-Acetoxy-4-hydroxybutanoic acid ethyl ester (0.5 g, 2.6 mmol) in pyridine (1 ml) was added to a solution of (4-methylphenyl)sulphonyl chloride (0.53 g, 2.76 mmol) in pyridine (1 ml) at 5°. After 16 h at 5° ethyl acetate and water were added, the organic layer was separated, washed with hydrochloric acid (2N), dried (MgSO$_4$) and the solvent evaporated to give the sub-title ester (0.8 g).

nmr δ(CDCl$_3$) 5.03 (1H, dd), 2.46 (3H, s), 2.04 (3H, s), 1.26 (3H, t);

m/z 344 (M+).

b) (S)-2-Hydroxy-4-((1-methylethyl)thio)butanoic acid

The product of step a) (0.78 g, 2.26 mmol) was added to a solution of 2-propanethiol (0.72 g, 9.6 mmol) and sodium (0.11 g, 4.8 mmol) in ethanol (6 ml). After stirring for 22 h the solvent was evaporated and the residue dissolved in ethyl acetate/water. The aqueous layer was separated, acidified with hydrochloric acid (2N) and extracted with ethyl acetate. The organic layer was dried (MgSO$_4$) and the solvent evaporated to give the sub-title acid (0.3 g).

nmr δ(CDCl$_3$) 4.44 (1H, dd), 1.28 (6H, d);

m/z 322 (M+ for DiTMS).

c) 2(S)-(3-(Acetylthio)-2(S)-methyl-1-oxopropoxy)-4-((1-methylethyl)thio)butanoic acid Prepared by the method of Example 28a).

m/z 322 (M+).

d) 2(S)-(3-Mercapto-2(S)-methyl-1-oxopropoxy)-4-((1-methylethyl)thio)butanoic acid 1-adamantanamine salt The title salt was prepared by the method of Example 1c), mp 197°–198°.

EXAMPLE 34

2(R)-(3-Mercapto-2(S)-methyl-1-oxopropoxy)-3-((2-methylpropyl)thio)propanoic acid 1-adamantanamine salt a) (R)-2-Hydroxy-3-((2-methylpropyl)thio)propanoic acid Prepared by the method of Example 12a).

nmr δ(CDCl$_3$) 4.43 (1H, dd), 3.03 (1H, dd), 2.90 (1H, dd), 2.49 (2H, d);

m/z 307 (M+ for DiTMS-15).

b) 2(R)-(3-(Acetylthio)-2(S)-methyl-1-oxopropoxy)-3-((2-methylpropyl)thio)propanoic acid Prepared by the method of Example 28a).

nmr δ(CDCl$_3$) 2.50 (2H, d), 2.33 (3H, s), 1.30 (3H, d), 0.99 (6H, d);

m/z 379 (M+ for TMS-15).

c) 2(R)-(3-Mercapto-2(S)-methyl-1-oxopropoxy)-3-((2-methylpropyl)thio)propanoic acid 1-adamantanamine salt The title salt was prepared by the method of Example 1c), mp 201°–202°.

EXAMPLE 35

3-(Cyclopentylmethoxy)-2(S)-(3-mercapto-2(S)-methyl-1-oxopropoxy)propanoic acid 1-adamantanamine salt a) (S)-4-((Cyclopentylmethoxy)methyl)-2,2-dimethyl-1,3-dioxolane Sodium hydride (0.63 g, 26.3 mmol) and cyclopentanemethanol (2.8 ml, 25.9 mmol) in dimethylformamide were heated at 50° for 30 min. The reaction mixture was cooled to 20° and (R)-2,2-dimethyl-1,3-dioxolane-4-methanol 4-methylbenzenesulphonate (5.0 g, 17.5 mmol) added. The reaction mixture was heated at 50° for 30 min and left at 20° for 18 h. Ether and brine were added, the organic layer dried (Na$_2$SO$_4$) and the solvent evaporated to give the sub-title ether (3.0 g).

nmr δ(CDCl$_3$) 4.26 (1H, q), 4.05 (1H, dd), 3.78 (1H, dd), 1.45 (3H, s), 1.38 (3H, s);

m/z 214 (M+).

b) (R)-3-(Cyclopentylmethoxy)-1,2-propanediol

The product of step a) (3.0 g, 13.9 mmol) was heated at 90° for 30 min in acetone (3.2 ml) and hydrochloric acid (1N, 8.7 ml). The acetone was evaporated and ethyl acetate/water added. The organic layer was separated, dried (MgSO$_4$) and the solvent evaporated to give the sub-title diol (1.6 g).

nmr δ(CDCl$_3$) 3.90 (1H, m), 3.70 (2H, m), 3.55 (2H, m), 2.10 (1H, m);

m/z 303 (M+ for DiTMS-15).

c) (S)-3-(Cyclopentylmethoxy)-2-hydroxypropanoic acid

Prepared by the method of Example 9a).

nmr δ(CDCl$_3$) 4.37 (1H, t), 3.80 (2H, m), 3.40 (2H, m);

m/z 332 (M+ for DiTMS).

d) 2(S)-(3-(Acetylthio)-2(S)-methyl-1-oxopropoxy)-3-(cyclopentylmethoxy)propanoic acid Prepared by the method of Example 28a).

nmr δ(CDCl$_3$) 5.30 (1H, m), 2.36 (1H, s), 1.30 (3H, d);

m/z 404 (M+ for TMS).

e) 3-(Cyclopentylmethoxy)-2(S)-(3-mercapto-2(S)-methyl-1-oxopropoxy)propanoic acid 1-adamantanamine salt The title salt was prepared by the method of Example 1c), mp 196°–197°.

EXAMPLE 36

2(R)-(3-Mercapto-2(S)-methyl-1-oxopropoxy)-3-((2,2,2-trifluoroethyl)thio)propanoic acid 1-adamantanamine salt a) (R)-2-Hydroxy-3-((2,2,2-trifluoroethyl)thio)-propanoic acid Prepared by the method of Example 12a).
nmr δ(CDCl$_3$) 4.52 (1H, q), 3.30 (2H, q);
m/z 204 (M+).

b) 2(R)-(3-(Acetylthio)-2(S)-methyl-1-oxopropoxy)-3-((2,2,2-trifluoroethyl)thio)propanoic acid Prepared by the method of Example 28a).
nmr δ(CDCl$_3$) 5.35 (1H, dd), 2.34 (3H, s), 1.30 (3H, d);
m/z 405 (M+ for TMS-15).

c) 2(R)-(3-Mercapto-2(S)-methyl-1-oxopropoxy)-3-((2,2,2-trifluoroethyl)thio)propanoic acid 1-adamantanamine salt The title salt was prepared by the method of Example 1c), mp 208°–209°.

EXAMPLE 37

2(S)-(3-Mercapto-2(S)-methyl-1-oxopropoxy)butanedioic acid 4-(1-methylethyl) ester 1-adamantanamine salt a) (S)-2-Hydroxybutanedioic acid 4-(1-methylethyl) 1-(2-propenyl) ester Prepared by the method of Example 13b).
nmr δ(CDCl$_3$) 4.70 (2H, d), 4.51 (1H, t), 1.24 (6H, d);
m/z 231 (M+ for TMS-45).

b) 2(S)-(3-(Acetylthio)-2(S)-methyl-1-oxopropoxy)-butanedioic acid 4-(methylethyl) 1-(2-propenyl) ester Prepared by the method of Example 12c).
nmr δ(CDCl$_3$) 5.51 (1H, t), 2.88 (2H, d), 2.33 (3H, s), 1.29 (3H, d);
m/z 360 (M+).

c) 2(S)-(3-(Acetylthio)-2(S)-methyl-1-oxopropoxy)-butanedioic acid 4-(1-methylethyl) ester Prepared by the method of Example 15d).
nmr δ(CDCl$_3$) 5.52 (1H, t), 2.91 (2H, d), 2.33 (3H, s);
m/z 392 (M+ for monoTMS).

d) 2(S)-(3-Mercapto-2(S)-methyl-1-oxopropoxy)-butanedioic acid 4-(1-methylethyl) ester 1-adamantanamine salt The title salt was prepared by the method of Example 1c), mp 177°–178°.

EXAMPLE 38

2(R)-(3-Mercapto-2(S)-methyl-1-oxopropoxy)-3-((1,1-dimethylpropyl)thio)propanoic acid 1-adamantanamine salt a) (R)-3-((1,1-Dimethylpropyl)thio)-2-hydroxy-propanoic acid 2-Methyl-2-butanethiol (5.5 ml, 40 mmol) and potassium hydroxide (2.47 g, 40 mmol) in methanol (40 ml) were added to a suspension of (S)-oxiranecarboxylic acid potassium salt (2.52 g, 20 mmol) in methanol (20 ml) at 0°. After stirring for 1 day at room temperature, the solvent was evaporated and the residue dissolved in water (15 ml) and hydrochloric acid (6N) to give a pH of 1.5. The product was extracted with ethyl acetate, dried (MgSO$_4$) and the solvent evaporated to give the sub-title compound (3.31 g).

nmr δ(CDCl$_3$) 4.45 (1H, q), 1.58 (2H, q), 0.95 (3H, t);
m/z 336 (M+ for DiTMS).

b) 2(R)-(3-(Acethylthio)-2(S)-methyl-1-oxopropoxy)-3-((1,1-dimethylpropyl)thio)propanoic acid Prepared by the method of Example 1b).
nmr δ(CDCl$_3$) 5.22 (1H, q), 2.34 (3H, s), 1.58 (2H, q), 0.95 (3H, t).

c) 2(R)-(3-Mercapto-2(S)-methyl-1-oxopropoxy)-3-((1,1-dimethylpropyl)thio)propanoic acid 1-adamantanamine salt The title salt was prepared by the method of Example 1c), mp 227°–228°.

EXAMPLE 39

2(S)-(3-Mercapto-2(S)-methyl-1-oxopropoxy)butanedioic acid 4-(2,2,2-trifluoroethyl) ester 1-adamantanamine salt a) (S)-2-Hydroxybutanedioic acid 4-(2,2,2-trifluoroethyl) ester Prepared by the method of Example 12b).
nmr δ(CDCl$_3$) 4.57 (3H, m), 2.97 (2H, m);
m/z 273 (M+ for TMS-15).

b) 2(S)-(3-(Acetylthio)-2(S)-methyl-1-oxopropoxy)-butanedioic acid 4-(2,2,2-trifluoroethyl) ester Prepared by the method of Example 28a).
nmr δ(CDCl$_3$) 5.57 (1H, dd), 2.36 (3H, s), 1.29 (3H, d).

c) 2(S)-(3-Mercapto-2(S)-methyl-1-oxopropoxy)-butanedioic acid 4-(2,2,2-trifluoroethyl) ester 1-adamantanamine salt The title salt was prepared by the method of Example 13e), mp 142°–143°.

EXAMPLE 40

2(R)-(3-Mercapto-2(S)-methyl-1-oxopropoxy)-3-(3-thienylthio)propanoic acid 1-adamantanamine salt a) (R)-2-Hydroxy-3-(3-thienylthio)propanoic acid Prepared by the method of Example 12a) using lithium 3-thienylthiolate.
nmr δ(CDCl$_3$) 4.44 (1H, dd), 3.38 (1H, dd), 3.18 (1H, dd);
m/z 348 (M+ for DiTMS).

b) 2(R)-(3-(Acetylthio)-2(S)-methyl-1-oxopropoxy)-3-(3-thienylthio)propanoic acid Prepared by the method of Example 28a).
nmr δ(CDCl$_3$) 5.23 (1H, dd), 3.36 (1H, dd), 3.25 (1H, dd), 2.36 (3H, s), 1.27 (3H, d);
m/z 420 (M+ for TMS).

c) 2(R)-(3-Mercapto-2(S)-methyl-1-oxopropoxy)-3-(3-thienylthio)propanoic acid 1-adamantanamine salt The title salt was prepared by the method of Example 1c), mp 189°–190°.

EXAMPLE 41

3-(Ethyl(methylsulphonyl)amino)-2(S)-(3-mercapto-2(S)-methyl-1-oxopropoxy)propanoic acid 1-adamantanamine salt a) (S)-3-(Ethyl(methylsulphonyl)amino)-2-hydroxypropanoic acid 2-propenyl ester Prepared by the method of Example 31a).
nmr δ(CDCl$_3$) 4.71 (2H, t), 4.40 (1H, m), 2.95 (3H, s), 1.27 (3H, t).

b) 2(S)-(3-(Acetylthio)-2(S)-methyl-1-oxopropoxy)-3-(ethyl(methylsulphonyl)amino)propanoic acid 2-propenyl ester Prepared by the method of Example 12c).
m/z 352 (M+-COCH$_3$).

c) 2(S)-(3-(Acetylthio)-2(S)-methyl-1-oxopropoxy)-3-(ethyl(methylsulphonyl)amino)propanoic acid
Prepared by the method of Example 15d).
nmr δ(CDCl$_3$) 5.30 (1H, t), 3.78 (2H, d), 2.90 (3H, s), 2.35 (3H, s), 1.35 (3H, d), 1.25 (3H, t).

d) 3-(Ethyl(methylsulphonyl)amino)-2(S)-(3-mercapto-2(S)-methyl-1-oxopropoxy)propanoic acid 1-adamantanamine salt
The title salt was prepared by the method of Example 1c), mp 195°–196°.

EXAMPLE 42

2(S)-(3-Mercapto-2(S)-methyl-1-oxopropoxy)-3-(methyl((1-methylethyl)sulphonyl)amino)propanoic acid 1-adamantanamine salt a) (S)-2-Hydroxy-3-(((1-methylethyl)sulphonyl)amino)propanoic acid 2-propenyl ester
Prepared by the method of Example 15b).
nmr δ(CDCl$_3$) 5.00 (1H, t), 4.17 (1H, t), 1.16 (6H, d).

b) (S)-2-Hydroxy-3-(methyl((1-methylethyl)sulphonyl)amino)propanoic acid 2-propenyl ester
Prepared by the method of Example 31a).
m/z 322 (M$^+$ for TMS-15).

c) 2(S)-(3-(Acetylthio)-2(S)-methyl-1-oxopropoxy)-3-(methyl((1-methylethyl)sulphonyl)amino)propanoic acid 2-propenyl ester
Prepared by the method of Example 12c).
nmr δ(CDCl$_3$) 2.99 (3H, s), 2.34 (3H, s).

d) 2(S)-(3-(Acetylthio)-2(S)-methyl-1-oxopropoxy)-3-(methyl((1-methylethyl)sulphonyl)amino)propanoic acid
Prepared by the method of Example 15d).
nmr δ(CDCl$_3$) 5.28 (1H, q), 3.00 (3H, s), 2.34 (3H, s); m/z 426 (M$^+$ for TMS-15).

e) 2(S)-(3-Mercapto-2(S)-methyl-1-oxopropoxy)-3-(methyl((1-methylethyl)sulphonyl)amino)propanoic acid 1-adamantanamine salt
The title salt was prepared by the method of Example 1c), mp 203°–204°.

EXAMPLE 43

2(S)-(3-Mercapto-2(S)-methyl-1-oxopropoxy)-3-((1-methylethyl)(methylsulphonyl)amino)propanoic acid 1-adamantanamine salt a) (S)-2-Hydroxy-3-((1-methylethyl)amino)propanoic acid 2-propenyl ester
2-Propanone (0.22 g, 3.7 mmol) was added to a solution of (S)-3-amino-2-hydroxypropanoic acid 2-propenyl ester hydrochloride (0.45 g, 2.5 mmol) and triethylamine (0.25 g, 2.5 mmol) in ethanol (2.5 ml). After 2 h the solution was cooled to 0° and sodium borohydride (0.15 g, 3.9 mmol) was added. After 20 min, water (0.4 ml) and dichloromethane were added. The mixture was filtered and the filtrate evaporated. The residue was dissolved in ether/water, the organic layer dried (MgSO$_4$) and the solvent evaporated to give the sub-title ester (0.15 g).
nmr δ(CDCl$_3$) 4.70 (2H, dd), 1.10 (6H, 2×d);
m/z 331 (M$^+$ for DiTMS).

b) (S)-2-Hydroxy-3-((1-methylethyl)(methylsulphonyl)amino)propanoic acid 2-propenyl ester
Prepared by the method of Example 15b).
nmr δ(CDCl$_3$) 4.38 (1H, t), 2.96 (3H, s), 1.30 (6H, d); m/z 322 (M$^+$ for TMS-15).

c) 2(S)-(3-(Acetylthio)-2(S)-methyl-1-oxopropoxy)-3-((1-methylethyl)(methylsulphonyl)amino)propanoic acid
Prepared by the method of Example 12c).
nmr δ(CDCl$_3$) 4.65 (2H, d), 2.91 (3H, s), 2.33 (3H, s), 1.32 (3H, d).

d) 2(S)-(3-(Acetylthio)-2(S)-methyl-1-oxopropoxy)-3-((1-methylethyl)(methylsulphonyl)amino)propanoic acid
Prepared by the method of Example 15d).
nmr δ(CDCl$_3$) 5.35 (1H, dd), 2.93 (3H, s), 2.33 (3H, s), 1.33 (3H, d);
m/z 370 ((M+1)$^+$).

e) 2(S)-(3-Mercapto-2(S)-methyl-1-oxopropoxy)-3-((1-methylethyl)(methylsulphonyl)amino)propanoic acid 1-adamantanamine salt
The title salt was prepared by the method of Example 1c), mp 189°–190°.

EXAMPLE 44

3-(Cyclopentylthio)-2(R)-(3-mercapto-2(S)-methyl-1-oxopropoxy)propanoic acid 1-adamantanamine salt a) (R)-3-(Cyclopentylthio)-2-hydroxypropanoic acid
Prepared by the method of Example 38a).
nmr δ(CDCl$_3$) 4.45 (1H, q), 3.00 (2×1H, dd);
m/z 319 (M$^+$ for DiTMS-15).

b) 2(R)-(3-(Acetylthio)-2(S)-methyl-1-oxopropoxy)-3-(cyclopentylthio)propanoic acid
Prepared by the method of Example 1b).
nmr δ(CDCl$_3$) 5.30 (1H, dd), 2.35 (3H, s), 1.32 (3H, d);
m/z 391 (M$^+$ for TMS-15).

c) 3-(Cyclopentylthio)-2(R)-(3-mercapto-2(S)-methyl-1-oxopropoxy)propanoic acid 1-adamantanamine salt
The title salt was prepared by the method of Example 1c), mp 218°–219°.

EXAMPLE 45

3-(2,2-Dimethyl-1-oxopropoxy)-2(S)-(3-mercapto-2(S)-methyl-1-oxopropoxy)propanoic acid 1-adamantanamine salt a) (S)-2,3-Dihydroxypropanoic acid 2-propenyl ester
Prepared by the method of Example 12b).
nmr δ(CDCl$_3$) 4.72 (2H, dd), 4.30 (1H, t);
m/z 290 (M$^+$ for DiTMS).

b) (S)-3-(((1,1-Dimethylethyl)dimethylsilyl)oxy)-2-hydroxypropanoic acid 2-propenyl ester
The product of step a) (3.5 g, 24 mmol), chloro(1,1-dimethylethyl)methylsilane (3.58 g, 24 mmol), triethylamine (4.9 ml, 24 mmol), 4-(dimethylamino)pyridine (0.115 g) in dichloromethane (80 ml) were stirred for 2 days. The reaction mixture was washed with water and ammonium chloride solution, dried (MgSO$_4$) and the solvent evaporated. Chromatography on silica with dichloromethane as eluant gave the sub-title alcohol (1.45 g).
nmr δ(CDCl$_3$) 4.62 (2H, dd), 0.80 (9H, s), 0.05 (6H, d);
m/z 317 (M$^+$ for TMS-15).

c) 2(S)-(3-(Acetylthio)-2(S)-methyl-1-oxopropoxy)-3-(((1,1-dimethylethyl)dimethylsilyl)oxy)propanoic acid 2-propenyl ester
Prepared by the method of Example 12c).
nmr δ(CDCl$_3$) 5.09 (1H, q), 2.27 (3H, s), 1.27 (3H, d), 0.82 (9H, s), 0.05 (6H, d);
m/z 389 (M$^+$ −15).

d) 2(S)-(3-(Acetylthio)-2(S)-methyl-1-oxopropoxy)-3-hydroxypropanoic acid 2-propenyl ester
The product of step c) (1.4 g, 34.6 mmol) and pyridinium (4-methylphenyl)sulphonate (0.512 g) in ethanol (25 ml) were heated at reflux for 20 h. The solvent was evaporated and the residue dissolved in ethyl acetate/brine. The organic extract was washed with water, dried (MgSO$_4$) and the solvent evaporated to give the sub-title alcohol (0.99 g).

nmr δ(CDCl$_3$) 5.19 (1H, q), 4.69 (2H, d), 2.34 (3H, s), 1.29 (3H, d);

m/z 362 (M+ for TMS).

e) 2(S)-(3-(Acetylthio)-2(S)-methyl-1-oxopropoxy)-3-(2,2-dimethyl-1-oxopropoxy)propanoic acid 2-propenyl ester Prepared by the method of Example 33a).

nmr δ(CDCl$_3$) 3.11 (2H, d), 2.79 (1H, q), 2.33 (3H, s), 1.32 (3H, d), 1.25 (9H, s);

m/z 374 (M+).

f) 2(S)-(3-(Acetylthio)-2(S)-methyl-1-oxopropoxy)-3-(2,2-dimethyl-1-oxopropoxy)propanoic acid Prepared by the method of Example 15d).

nmr δ(CDCl$_3$) 5.37 (1H, q), 2.79 (1H, q), 2.33 (3H, s), 1.31 (3H, d), 1.20 (9H, s).

g) 3-(2,2-Dimethyl-1-oxopropoxy)-2(S)-(3-mercapto-2(S)-methyl-1-oxopropoxy)propanoic acid 1-adamantanamine salt The title salt was prepared by the method of Example 13e), mp 185°–186°.

EXAMPLE 46

3-((1-Ethylpropyl)thio)-2(R)-(3-mercapto-2(S)-methyl-1-oxopropoxy)propanoic acid 1-adamantanamine salt a) (R)-3-((1-Ethylpropyl)thio)-2-hydroxypropanoic acid Prepared by the method of Example 38a).

nmr δ(CDCl$_3$) 4.41 (1H, q), 3.03 (1H, dd), 2.90 (1H, dd), 2.61 (1H, quin);

m/z 336 (M+ for DiTMS).

b) 2(R)-(3-(Acetylthio)-2(S)-methyl-1-oxopropoxy)-3-((1-ethylpropyl)thio)propanoic acid Prepared by the method of Example 1b).

nmr δ(CDCl$_3$) 5.25 (1H, q), 2.34 (3H, s), 1.31 (3H, d), 0.98 (6H, t);

m/z 393 (M+ for TMS-15).

c) 3-((1-Ethylpropyl)thio)-2(R)-(3-mercapto-2(S)-methyl-1-oxopropoxy)propanoic acid 1-adamantanamine salt The title salt was prepared by the method of Example 1c), mp 212°–213°.

EXAMPLE 47

2(R)-(3-Mercapto-2(S)-methyl-1-oxopropoxy)-3-(propylthio)propanoic acid 1-adamantanamine salt a) (R)-2-Hydroxy-3-(propylthio)propanoic acid Prepared by the method of Example 12a).

nmr δ(CDCl$_3$) 4.44 (1H, dd), 3.06 (1H, dd), 2.95 (1H, dd);

m/z 308 (M+ for DiTMS).

b) 2(R)-(3-(Acetylthio)-2(S)-methyl-1-oxopropoxy)-3-((1-ethylpropyl)thio)propanoic acid Prepared by the method of Example 28a).

nmr δ(CDCl$_3$) 5.27 (1H, dd), 3.03 (1H, dd), 2.97 (1H, dd), 2.60 (2H, t), 2.34 (3H, s), 1.31 (3H, d), 0.98 (3H, t).

c) 2(R)-(3-Mercapto-2(S)-methyl-1-oxopropoxy)-3-(propylthio)propanoic acid 1-adamantanamine salt The title salt was prepared by the method of Example 1c).

nmr δ(CD$_3$OD) 4.98 (1H, dd), 3.03 (1H, dd), 1.24 (3H, d), 0.98 (3H, t);

m/z 418 (M+1 for salt).

EXAMPLE 48

3-(Cyclopropylthio)-2(R)-(3-mercapto-2(S)-methyl-1-oxopropoxy)propanoic acid 1-adamantanamine salt a) Cyclopropanethiol lithium salt Bromocylopropane (7.16 g, 59 mmol) in ether (20 ml) was added to a stirred mixture of lithium wire (0.82 g, 119 mmol) in ether (20 ml), at 0° under nitrogen. The reaction was initiated by the addition of iodine (1 crystal) and was complete in 2 h. Sulphur (1.9 g, 59 mmol) was added and after 30 min at room temperature, the solvent was evaporated to give the sub-title salt.

b) (R)-3-(Cyclopropylthio)-2-hydroxypropanoic acid

Prepared by the method of Example 12a) using the lithium salt of step a).

nmr δ(CDCl$_3$) 4.49 (1H, q), 3.14 (1H, dd), 2.97 (1H, dd);

m/z 162 (M+).

c) 2(R)-(3-(Acetylthio)-2(S)-methyl-1-oxopropoxy)-3-(cyclopropylthio)propanoic acid Prepared by the method of Example 28a).

nmr δ(CDCl$_3$) 5.36 (1H, dd), 2.34 (3H, s), 1.32 (3H, d);

m/z 378 (M+ for TMS).

d) 3-(Cyclopropylthio)-2(R)-(3-mercapto-2(S)-methyl-1-oxopropoxy)propanoic acid 1-adamantanamine salt The title salt was prepared by the method of Example 1c).

nmr δ(CD$_3$OD) 5.11 (1H, dd), 3.16 (1H, dd), 2.90 (1H, dd), 1.25 (3H, d), 0.87 (2H, m), 0.50 (2H, m);

m/z 263 ((M−1)+).

EXAMPLE 49

α(S)-(2(S)-(((1,1-Dimethylethoxy)carbonyl)amino)-3-mercapto-1-oxopropoxy)benzenepropanoic acid 1-adamantanamine salt a) N-((1,1-Dimethylethoxy)carbonyl)-D-cysteine acetate ester Diethyl azodicarboxylate (6.3 ml, 40 mmol) was added to a stirred solution of triphenylphosphine (10.49 g, 40 mmol) in acetonitrile (200 ml) and tetrahydrofuran (100 ml) at −45°. After 30 min a solution of N-((1,1-dimethylethoxy)carbonyl)-D-serine (8.2 g, 40 mmol) in acetonitrile (100 ml) was added over 45 min. After stirring for 2 h at −25° and 1 h at room temperature, the solution was cooled to −40° and a solution of caesium carbonate (6.5 g, 40 mmol) and ethanethioic acid (3.04 g, 40 mmol) in dimethylformamide (50 ml) was added. After 1 h at room temperature, the solvent was evaporated and the residue dissolved in ethyl acetate and water. The aqueous layer was separated, acidified to pH 4 with potassium hydrogen sulphate solution and extracted with ethyl acetate. The organic extract was dried (MgSO$_4$) and the solvent evaporated. Chromatography on silica with ethyl acetate/dichloromethane mixtures as eluant gave the sub-title compound (3.8 g).

nmr δ(CDCl$_3$) 2.37 (3H, s), 1.45 (9H, s);

m/z 408 ((M+1)+ for DiTMS).

b) α(S)-Hydroxybenzenepropanoic acid 2-propenyl ester

Prepared by the method of Example 13b) using 3-bromo-1-propene and caesium carbonate.

nmr δ(CDCl$_3$) 4.48 (1H, q), 3.14 (1H, dd), 2.98 (1H, dd);

m/z 263 (M+ for TMS-15).

c) α(S)-(3-(Acetylthio)-2(S)-(((1,1-dimethylethoxy)carbonyl)amino)-1-oxopropoxy)benzenepropanoic acid 2-propenyl ester Prepared by the method of Example 12c).
nmr δ(CDCl$_3$) 4.60 (2H, d), 2.31 (3H, s), 1.43 (9H, s); m/z 452 ((M+1)+).

d) α(S)-(3-(Acetylthio)-2(S)-(((1,1-dimethylethoxy)carbonyl)amino)-1-oxopropoxy)benzenepropanoic acid Prepared by the method of Example 15d).
nmr δ(CDCl$_3$) 4.50 (1H, m), 2.31 (3H, s), 1.42 (9H, s); m/z 412 ((M+1)+).

e) α(S)-(2(S)-(((1,1-Dimethylethoxy)carbonyl)amino)-3-mercapto-1-oxopropoxy)benzenepropanoic acid 1-adamantanamine salt The title salt was prepared by the method of Example 13e), mp 190° decomposes.

EXAMPLE 50

α(S)-(2(S)-Amino-3-mercapto-1-oxopropoxy)benzenepropanoic acid 1-adamantanamine salt α(S)-(2(S)-(((1,1-Dimethylethoxy)carbonyl)amino)-3-mercapto-1-oxopropoxy)benzenepropanoic acid (0.3 g) was stirred for 1 h in dichloromethane (5 ml) and trifluoroacetic acid (5 ml). The solvent was evaporated and the residue triturated with ether/dichloromethane/methanol and filtered to give the title salt (0.13 g), mp 165°–166°.

EXAMPLE 51

α(S)-(5(S)-(Benzoylamino)-1,4-dioxo-6-phenylhexyloxy)benzenepropanoic acid 1-adamantanamine salt α(S)-(5(S)-(Benzoylamino)-1,4-dioxo-6-phenylhexyloxy)benzenepropanoic acid phenylmethyl ester Prepared by the method of Example 12c).
nmr δ(CDCl$_3$) 5.27 (1H, q), 5.14 (2H, 2xq), 5.0 (1H, quin);
m/z 564 ((M+1)+).

b) α(S)-(5(S)-(Benzoylamino)-1,4-dioxo-6-phenylhexyloxy)benzenepropanoic acid 1-adamantanamine salt The product of step a) (0.26 g, 0.46 mmol) in dioxan (35 ml) was hydrogenated at 4 bar over 10% palladium on charcoal for 1 day. The catalyst was filtered off and the solvent evaporated. The residue was dissolved in ethyl acetate (5 ml), and 1-adamantanamine (0.07 g, 0.46 mmol) in ethyl acetate (5 ml) was added. The resulting solid was filtered off to give the title salt (0.2 g), mp 172°–174°.

EXAMPLE 52

2(S)-(5(S)-(Benzoylamino)-1,4-dioxo-6-phenylhexyloxy)-4-methylpentanoic acid 1-adamantanamine salt a) 2(S)-(5(S)-(Benzoylamino)-1,4-dioxo-6-phenylhexyloxy)-4-methylpentanoic acid phenylmethyl ester Prepared by the method of Example 12c).
nmr δ(CDCl$_3$) 2.70 (2H, t), 0.91 (6H, t);
m/z 530 ((M+1)+).

b) 2(S)-(5(S)-(Benzoylamino)-1,4-dioxo-6-phenylhexyloxy)-4-methylpentanoic acid 1-adamantanamine salt The title salt was prepared by the method of Example 51b), mp 157°–159°.

EXAMPLE 53

α(S)-(5(S)-(Benzoylamino)-1,4-dioxo-6-phenylhexyloxy)cyclohexanepropanoic acid 1-adamantanamine salt a) α(S)-Hydroxycyclohexanepropanoic acid phenylmethyl ester Prepared by the method of Example 13b).
nmr δ(CDCl$_3$) 5.20 (2H, s), 2.72 (1H, d), 1.80 (1H, d); m/z 319 (M+ for TMS-15).

b) α(S)-(5(S)-(Benzoylamino)-1,4-dioxo-6-phenylhexyloxy)cyclohexanepropanoic acid phenylmethyl ester Prepared by the method of Example 12c).
nmr δ(CDCl$_3$) 3.30 (1H, dd), 3.15 (1H, dd), 2.70 (1H, t);
m/z 570 (M+1)+).

c) α(S)-(5(S)-(Benzoylamino)-1,4-dioxo-6-phenylhexyloxy)cyclohexanepropanoic acid 1-adamantanamine salt The title salt was prepared by the method of Example 51b), mp 173°–175°.

EXAMPLE 54

α(S)-(5-(Benzoylamino)-1,4-dioxo-6-phenylhexyloxy)-4-nitrobenzenepropanoic acid 1-adamantanamine salt The title salt was prepared by the method of Example 1b), with a reaction time of 24 h at reflux temperature, mp 162°–163°.

EXAMPLE 55

α(S)-((2-(1(S)-Carboxy-2-phenylethoxy)-1(S)-methyl-2-oxoethyl)amino)benzenebutanoic acid a) 4(S)-Methyl-2,5-dioxo-α(S)-(2-phenylethyl)oxazolidineacetic acid phenylmethyl ester Bis-(trichloromethyl)carbonate (0.87 g, 2.9 mmol) was added to a stirred mixture of α(S)-((1(S)-carboxyethyl)-amino)benzenebutanoic acid phenylmethyl ester (2.5 g, 7.3 mmol) in dichloromethane (100 ml). After heating at reflux for 20 h the solvent was evaporated to give the sub-title compound.

nmr δ(CDCl$_3$) 5.19 (2H, s), 4.40 (1H, q), 4.30 (1H, q), 1.48 (3H, d);
m/z 368 ((m+1)+).

b) α(S)-((1(S)-Methyl-2-oxo-2-(2-oxo-2-(phenylmethoxy)-1(S)-(phenylmethyl)ethoxy)ethyl)amino)benzenebutanoic acid phenylmethyl ester The product of step a) 0.5 g, 1.36 mmol) and α(S)-hydroxybenzenepropanoic acid phenylmethyl ester (0.53 g, 2.07 mmol) were heated at reflux for 20 h in toluene (40 ml) containing 4-(dimethylamino) pyridine (catalytic). The solvent was evaporated and the residue chromatographed on silica with ethyl acetate as eluant to give the sub-title compound (0.56 g).

nmr δ(CDCl$_3$) 5.33 (1H, q), 3.40 (1H, q), 3.28 (1H, t), 1.25 (3H, d);
m/z 580 (M+1)+).

c) α(S)-((2-(1(S)-Carboxy-2-phenylethoxy)-1(S)-methyl-2-oxoethyl)amino benzenebutanoic acid The product of step b) (0.5 g) in ethyl acetate (30 ml) and trifluoroacetic acid (2 ml) was hydrogenated at 1 bar over 10% palladium on charcoal for 1 day. The catalyst was filtered off, the solvent evaporated and the residue purified by reverse phase HPLC with water/methanol mixtures as eluant, to give the title acid (0.14 g), mp 199°–200°.

EXAMPLE 56

2(S)-(5(S)-(Benzoylamino)-1,4-dioxo-6-phenylhexyloxy)-3-(phenylmethoxy)propanoic acid a) (S)-2-Hydroxy-3-(phenylmethoxy)propanoic acid 2-propenyl ester Prepared by the method of Example 13b).

nmr δ(CDCl$_3$) 4.70 (2H, dd), 4.60 (2H, q), 4.33 (1H, t), 3.30 (2H, t);
m/z 236 (M+).

b) 2(S)-(5(S)-(Benzoylamino)-1,4-dioxo-6-phenylhexyloxy)-3-(phenylmethoxy)propanoic acid 2-propenyl ester Prepared by the method of Example 12c).
m/z 544 ((M+1)+).

c) 2(S)-(5)-(Benzoylamino)-1,4-dioxo-6-phenylhexyloxyl)-3-(phenylmethoxy)propanoic acid The title acid was prepared by the method of Example 12d), mp 144°–145°.

EXAMPLE 57

2(S)-(5(S)-(Benzoylamino)-1,4-dioxo-6-phenylhexyloxy)hexanoic acid 1-adamatanamine salt a) 2(S)-(5(S)-(Benzoylamino)-1,4-dioxo-6-phenylhexyloxy)hexanoic acid phenylmethyl ester Prepared by the method of Example 12c).
nmr δ(CDCl$_3$) 5.18 (2H, q), 2.70 (2H, t), 0.86 (3H, t); m/z 530 (M+1)+).

b) 2(S)-(5(S)-(Benzoylamino)-1,4-dioxo-6-phenylhexyloxyl)hexanoic acid 1-adamantanamine salt The title salt was prepared by the method of Example 51b, mp 156°–158°.

EXAMPLE 58

4-Amino-α(S)-(5-(benzoylamino)-1,4-dioxo-6-phenylhexyloxy)benzenepropanoic acid 1-adamantanamine salt a) α(S)-Hydroxy-4-nitrobenzenepropanoic acid phenylmethyl ester Prepared by the method of Example 13b.
nmr δ(CDCl$_3$) 8.06 (2H, d), 4.54 (1H, q), 3.23 (1H, dd), 3.08 (1H, dd);
m/z 373 (M+ for TMS).

b) α(S)-(5(Benzoylamino)-1,4-dioxo-6-phenylhexyloxy)-4-nitrobenzenepropanoic acid phenylmethyl ester Prepared by the method of Example 12c).
nmr δ(CDCl$_3$) 8.05 (2H, dd), 6.70 (1H, dd), 5.34 (1H, q), 5.16 (1H, dd), 5.10 (1H, dd);
m/z 609 (M+1)+).

c) 4-Amino-α(S)-(5-(benzoylamino)-1,4-dioxo-6-phenylhexyloxy)benzenepropanoic acid 1-adamantanamine salt The title compound was prepared by the method of Example 55c) as the free acid and converted to the 1-adamantanamine title salt, mp 166°–167°.

EXAMPLE 59

2(S)-(5(S)-Benzoylamino)-1,4-dioxo-6-phenylhexyloxy)-3(dimethylamino)propanoic acid trifluoroacetate salt a) (S)-3-(Dimethylamino)-2-hydroxypropanoic acid Formaldehyde (2 ml of 38% aqueous solution) was added to a stirred mixture of (S)-3-amino-2-hydroxypropanoic acid (0.419 g, 3.99 mmol), concentrated hydrochloric acid (0.59 ml) and water (10 ml) at 0°. After 10 min, sodium borohydride (1.308 g, 34.6 mmol) was added over 50 min. Further formaldehyde (2 ml of 38% aqueous solution) was added over 35 min followed by concentrated hydrochloric acid over 25 min. After 1.75 h at 0°–10° the pH was adjusted to 6–7 with sodium hydroxide (2N). The water was evaporated and the residue treated with ethanol. The solution was filtered and the ethanol evaporated three times to give the sub-title compound.

nmr δ(D$_2$O) 4.23 (1H, dd), 3.24 (1H, dd), 3.12 (1H, dd), 2.77 (6H, s);
m/z 134 ((M+1)+).

b) (S)-3-(Dimethylamino)-2-hydroxypropanoic acid phenylmethyl ester hydrochloride salt Prepared by the method of Example 12b).
nmr δ(d$_6$-DMSO) 5.19 (2H, s), 2.78 (6H, s).

c) 2(S)-(5(S)-(Benzoylamino)-1,4-dioxo-6-phenylhexyloxy)-3-(dimethylamino)propanoic acid phenylmethyl ester Prepared by the method of Example 12c).
nmr δ(CDCl$_3$) 5.19 (2H, 2xd), 2.36 (6H, s);
m/z 531 ((M+1)+).

d) 2(S)-(5(S)-(Benzoylamino)-1,4-dioxo-6-phenylhexyloxy)-3-(dimethylamino)propanoic acid trifluoroacetate salt The title salt was prepared by the method of Example 51b), and purified by HPLC, mp 93°–94°.

EXAMPLE 60

α(S)-(2(S)-((Hydroxy(4-phenylbutyl)phosphinyl)oxy)-1-oxopropoxy)benzenepropanoic acid Di-(1-adamantanamine) salt a) α(S)-Hydroxybenzenepropanoic acid diphenylmethyl ester Prepared by the method of Example 13b). nmr δ(CDCl$_3$) 6.94 (1H, s), 4.57 (1H, t), 2.70 (1H, s).

b) α(S)-(2(S)-(2,2-Dichloroacetyloxy)-1-oxopropoxy)-benzenepropanoic acid diphenylmethyl ester Prepared by the method of Example 12c).
nmr δ(CDCl$_3$) 6.87 (1H, s), 5.95 (1H, s), 5.48 (1H, q), 5.21 (1H, q), 1.48 (3H, d);
m/z 515 ((M+1)+).

c) α(S)-(2(S)-Hydroxy-1-oxopropoxy)benzenepropanoic acid diphenylmethyl ester

The product of step b) (0.556 g, 1.08 mmol) and lithium hydroxide monohydrate (0.041 g, 1.08 mmol) were stirred at 0° for 1 h in dioxan (10 ml) and water (3 ml). Ethyl acetate and sodium bicarbonate solution were added and the organic layer separated, dried (MgSO$_4$) and the solvent evaporated. Chromatography on silica with ethyl acetate/petroleum ether (60°–80°) as eluant gave the sub-title compound (0.3 g).

nmr δ (CDCl$_3$) 6.89 (1H, s), 2.57 (1H, d), 1.25 (3H, d);
m/z 489 ((M+Rb)+).

d) α(S)-(1-Oxo-2(S)-(((4-phenylbutyl)phosphinyl)oxy)propoxy)benzenepropanoic acid diphenylmethyl ester Prepared by the method of Example 12c).
nmr δ (CDCl$_3$) 6.87 (1H, s), 5.43 (1H, q);
m/z 585 ((M+1)+).

e) α(S)-(2(S)-((Hydroxy(4-phenylbutyl)phosphinyl)oxy)-1-oxopropoxy)benzenepropanoic acid diphenylmethyl ester Sodium periodate (0.223 g, 1.03 mmol) in water (4 ml) was added dropwise over 10 min to a stirred suspension of the product of step d) (0.55 g, 0.94 mmol) in dioxan (10 ml). After stirring for 20 h, water and ethyl acetate were added. The organic layer was separated, washed with potassium hydrogen sulphate solution, dried (MgSO$_4$) and the solvent evaporated. Trituration with ether gave the sub-title compound (0.17 g).

nmr δ (d$_6$-DMSO) 6.79 (1H, s), 5.43 (1H, m), 1.29 (3H, d).

f) α(S)-(2(S)-((Hydroxy(4-phenylbutyl)phosphinyl)oxy)-1-oxopropoxy)benzenepropanoic acid Di-(1-adamantanamine) salt

EXAMPLE 61

2(R)-(3-Mercapto-2(S)-methyl-1-oxopropoxy)-3-(methylthio)propanoic acid sodium salt The title salt was prepared by the method of Example 51b), at atmospheric pressure, mp 177°–180°.

The free acid, prepared by the method of Example 1c), (0.63 g) was added to water (150 ml) containing sodium hydrogen carbonate (0.222 g). The resulting solution was freeze-dried to give the title salt as a colourless solid.

nmr δ (D$_2$O) 5.05 (1H, dd), 2.20 (3H, s), 1.30 (3H, d); m/z 261 ((M+Na+1)$^+$).

EXAMPLE 62

2(R)-(3-Mercapto-2(S)-methyl-1-oxopropoxy)-3-(methylthio)propanoic acid calcium salt The free acid, prepared by the method of Example 1c), (0.24 g) was dissolved in methanol (10 ml) and calcium acetate (0.079 g) was added. After heating at reflux for 45 min the solvent was evaporated and the residue azeotroped with toluene repeatedly, to remove acetic acid. Trituration with ether/dichloromethane gave the title salt as a colourless solid, mp 169°–178°.

EXAMPLE 63

2(R)-(3-Mercapto-2(S)-methyl-1-oxopropoxy)-3-(methylthio)propanoic acid magnesium salt Prepared by the method of Example 62a), using the free acid (0.31 g) and magnesium acetate tetrahydrate (0.14 g), to give the title salt, mp 198°–203°.

EXAMPLE 64

2(R)-(3-Mercapto-2(S)-methyl-1-oxopropoxy)-3-(methylthio)propanoic acid L-lysine salt The free acid, prepared by the method of Example 1c), (0.23 g) was dissolved in methanol (10 ml) and L-lysine (0.14 g) added. After stirring for 1 h, the solvent was evaporated. Trituration with ether/dichloromethane gave the title salt, mp 125°–133°.

EXAMPLE 65

2(R)-(3-Mercapto-2(S)-methyl-1-oxopropoxy)-3-(methylthio)propanoic acid L-arginine salt The free acid, prepared by the method of Example 1c), (0.25 g) was dissolved in methanol (10 ml) and L-arginine (0.18 g) added. After sonication to give a clear solution, the solvent was evaporated and the residue triturated with ether/dichloromethane to give the title salt as a colourless solid, mp 80°–95°.

EXAMPLE X

In Vitro Assay of Inhibitors of Angiotensin Converting Enzyme

The method is based upon that of Cushman and Cheung (1971) but uses a radioactive substrate [glycine-1-$^{14}$C]hippuryl-L-histidyl-L-leucine (HHL) whose hydrolysis may be determined by liquid scintillation counting of released [$^{14}$C]-hippuric acid. Hydrolysis of 2 mM HHL by an extract of rabbit lung acetone powder (Sigma) over a 30 min. incubation period at 37° is followed by acidification of the reaction mixture and extraction of [$^{14}$C]hippurate with ethyl acetate.

Potential inhibitors are tested initially at 0.01 mM and if found active are retested at lower concentrations to determine an IC$_{50}$. Dimethyl sulphoxide at 1% final concentration may be used as a solubility aid without affecting enzyme activity. Compounds of specific interest are studied at a range of substrate and inhibitor concentrations to determine the type of inhibition and are also tested against other enzymes, eg carboxypeptidase A to establish their specificity for ACE.

EXAMPLE Y

Efficacy and duration of action were investigated in urethane anaesthetised rats of the Sprague-Dawley strain. Percentage changes in the pressor response to intravenous bolus administration of angiotensin I (100–600 ng/kg) were recorded and compared to pre-dose control values.

EXAMPLE Z

The rate of onset of action of the compounds was investigated by their rate of hydrolysis in human blood. Hydrolysis was followed by measurement of the acid produced after incubation with human blood. The compound (20 μM) was incubated with human blood at 37° and samples taken at suitable time intervals. Further hydrolysis was stopped and the blood denatured by the addition of 11 volumes of cold methanol. Protein was removed by centrifugation and the products analysed by HPLC. In the case of thiol containing esters an aliquot of the supernatant was taken for derivatisation of the thiol group by N-pyrene maleimide, after the method of Pereira et al, *J. Chromatog.*, 1988, 425, 208–213. The derivatised products were loaded onto AASP C18 cassettes and the products analysed by reverse phase HPLC. Products were quantified by comparison with a set of standards which had been spiked into denatured human blood and treated as above.

We claim:

1. Compounds of formula I, $Z(CH_2)_nCHR_1COOCHR_2COOH$ in which Z is —SR$_3$,

R$_1$ is hydrogen, alkyl C$_{1-6}$, NHR$_8$ or (CH$_2$)$_p$R$_9$,

R$_2$ is (CH$_2$)$_m$XR$_{10}$,

X is O, S(O)$_q$, C=O or NR$_{11}$, and

R$_{10}$ is alkyl C$_{1-6}$, alkylhalo C$_{1-6}$, alkoxy C$_{1-6}$, alkoxy C$_{1-6}$ substituted by halogen, alkanoyl C$_{1-6}$, S(O)$_r$R$_{12}$, NR$_{13}$R$_{14}$, phenyl, alkylphenyl C$_{7-12}$, naphthalenyl or a 5-membered unsaturated heterocyclic ring, n is an integer from 0 to 6, m and p, which may be the same or different, are each an integer from 1 to 6, R$_9$ is hydrogen, SR$_{15}$ or phenyl optionally substituted by OR$_{16}$, R$_3$ and R$_{15}$, which may be the same or different, are each hydrogen or alkanoyl C$_{1-6}$, R$_8$ is hydrogen or COOR$_{17}$, q and r, which may be the same or different, are each 0, 1, or 2, R$_{11}$, R$_{13}$, R$_{14}$, R$_{16}$, and R$_{17}$, which may be the same or different, are each hydrogen or alkyl C$_{1-6}$, and R$_{12}$ is hydrogen, alkyl C$_{1-6}$ or phenyl, and pharmaceutically acceptable salts thereof.

2. A compound of formula I, as defined in claim 1, or a pharmaceutically acceptable salt thereof, wherein X is S or O.

3. A compound of formula I, as defined in claim 1, or a pharmaceutically acceptable salt thereof, wherein R$_1$ is methyl.

4. A compound of formula I, as defined in claim 1, or a pharmaceutically acceptable salt thereof, wherein $R_{10}$ is alkyl $C_{1-6}$.

5. A compound of formula I, as defined in claim 1, which is
   2(R)-(3-Mercapto-2(S)-methyl-1-oxopropoxy)-3-(methylthio)propanoic acid,
   2(S)-2-(3-Mercapto-2(S)-methyl-1-oxopropoxy)-3-methoxypropanoic acid,
   2(R)-(3-Mercapto-2(S)-methyl-1-oxopropoxy)-3-((1-methylethyl)thio)propanoic acid, or a pharmaceutically acceptable salt thereof.

6. A pharmaceutical composition comprising a compound of formula I, as defined in claim 1, or a pharmaceutically acceptable salt thereof, in association with a pharmaceutically acceptable carrier, diluent or adjuvant.

7. A compound of formula I, as defined in claim 1, which is
   2(R)-(3-Mercapto-2(S)-methyl-1-oxopropoxy)-3-(phenylthio)propanoic acid,
   2(S)-(3-Mercapto-2(S)-methyl-1-oxopropoxy)-3-(phenylmethoxy)propanoic acid,
   2(S)-(3-Mercapto2(S)-methyl-1-oxopropoxy)-4-(methylthio)butanoic acid,
   3-Ethoxy-2(S)-(3-mercapto-2(S)-methyl-1-oxopropoxy)propanoic acid,
   2(S)-(3-Mercapto-2(S)-methyl-1-oxopropoxy)-3-(1-methylethoxy)propanoic acid,
   2(S)-(3-Mercapto-2(S)-methyl-1-oxopropoxy)-3-phenoxypropanoic acid,
   3-(1,1-Dimethylethoxy)-2(S)-(3-mercapto-2(S)-methyl-1-oxopropoxy)propanoic acid,
   2(R)-(3-Mercapto-2(S)-methyl-1oxopropoxy)-3-(phenylsulphonyl)propanoic acid,
   3-(Ethylthio)-2(R)(3-mercapto-2(S)-methyl-1-oxopropoxy)propanoic acid,
   2(S)-(3-Mercapto-2(S)-methyl-1-oxopropoxy)-butanedioic acid 4-methyl ester,
   2(R)-(3-Mercapto-2(S)-methyl-1-oxopropoxy)-3-((phenylmethyl)thio)propanoic acid,
   2(S)-(3-Mercapto-2(S)-methyl-1-oxopropoxy)-3-((methylsulphonyl)amino)propanoic acid,
   3-(Acetylamino)2(S)-(3-mercapto-2(S)-methyl-1-oxopropoxy)propanoic acid,
   4-Amino-2(S)-(3-mercapto-2(S)-methyl-1-oxopropoxy)-4-oxobutanoic acid,
   3-((1,1-Dimethylethyl)thio)-2(R)-(3-mercapto-2(S)-methyl-1-oxopropoxy)propanoic acid,
   2(R)-(3-Mercapto-2(S)-methyl-1-oxopropoxy)-3-(1-naphthalenylthio)propanoic acid,
   2(S)-(3-Mercapto-1-oxopropoxy)-3-(phenylmethoxy)propanoic acid,
   2(S)-(3-Mercapto-2(S)-methyl-1-oxopropoxy)-3-((phenylsulphonyl)amino)propanoic acid,
   2(R)-(3-Mercapto-2(S)-methyl-1-oxopropoxy)-3-(2-thienylethio)propanoic acid,
   2(S)-(3-Mercapto-2(S)-methyl-1-oxopropoxy)-3-(methyl(methylsulphonyl)amino)propanoic acid,
   2(S)-(3-Mercapto-2(S)-methyl-1-oxopropoxy)-4-phenoxybutanoic acid,
   2(S)-(3-Mercapto-2(S)-methyl-1-oxopropoxy)-4-((1-methylethyl)thio)butanoic acid,
   2(R)-(3-Mercapto-2(S)-methyl-1-oxopropoxy)-3-((2-methylpropyl)thio)propanoic acid,
   3-(Cyclopentylmethoxy)-2(S)-(3-mercapto-2(S)-methyl-1-oxopropoxy)propanoic acid,
   2(R)-(3-Mercapto-2(S)-methyl-1-oxopropoxy)-3((2,2,2,-trifluoroethyl)thio)propanoic acid,
   2(S)-(3-Mercapto-2(S)-methyl-1-oxopropoxy)-butanedioic acid 4-(1-methylethyl) ester,
   2(R)-(3-Mercapto-2(S)-methyl-1-oxopropoxy)-3-((1,1-dimethylpropyl)thio)propanoic acid,
   2(S)-(3-Mercapto-2(S)-methyl-1-oxopropoxy)-butanedioic acid 4-(2,2,2,-trifluoroethyl) ester,
   2(R)-(3-Mercapto-2(S)-methyl-1-oxopropoxy)-3-(3-thienylthio)propanoic acid,
   3-(Ethyl(methylsulphonyl)amino)-2(S)-(3-mercapto-2(S)-methyl-1-oxopropoxy)propanoic acid,
   2(S)-(3-Mercapto-2(S)-methyl-1-oxopropoxy)-3-(methyl((1-methylethyl)sulphonyl)amino)propanoic acid,
   2(S)-(3-Mercapto-2(S)-methyl-1-oxopropoxy)-3-((1-methylethyl)(methylsulphonyl)amino)propanoic acid,
   3-(Cyclopentylthio)2(R)-(3-mercapto-2(S)-methyl-1-oxopropoxy)propanoic acid,
   3-(2,2-Dimethyl-1-oxopropoxy)-2(S)-(3-mercapto-2(S)-methyl-1-oxopropoxy)propanoic acid,
   3-1-Ethylpropylthio)-2(R)-(3-mercapto-2(S)-methyl-1-oxopropoxy)propanoic acid,
   2(R)-(3-Mercapto-2(S)-methyl-1-oxopropoxy)-3-(propylthio)propanoic acid,
   3-(Cyclopropylthio)-2(R)-(3-mercapto-2(S)-methyl-1-oxopropoxy)propanoic acid,
   or a pharmaceutically acceptable salt thereof.

* * * * *

UNITED STATES PATENT AND TRADEMARK OFFICE
CERTIFICATE OF CORRECTION

PATENT NO. : 5,348,978

DATED : September 20, 1994

INVENTOR(S) : ANDREW J.G. BAXTER ET AL.

It is certified that error appears in the above-identified patent and that said Letters Patent is hereby corrected as shown below:

Column 22, line 1, "(Acethylthio)" should be --(Acetylthio)--

Column 25, line 58, "((1-ethylpropyl)thio)" should be --(propylthio)--

Column 27, line 33, before "$a$(S)-(5(S)-..." insert -- a) --

Column 28, line 51, "M(+1)$^+$)" should be --((M+1)$^+$)--

Column 29, line 2, "3.30" should be --3.80--

Column 29, line 9, "2(S)-(5)-..." should be -- 2(S)-(5(S)-... --

Column 29, line 22, "(M+1)$^+$)" should be --((M+1)$^+$)--

Column 29, line 43, "(M+1)$^+$)" should be --((M+1)$^+$)--

UNITED STATES PATENT AND TRADEMARK OFFICE
CERTIFICATE OF CORRECTION

PATENT NO. : 5,348,978

DATED : September 20, 1994

INVENTOR(S) : ANDREW J.G. BAXTER ET AL.

It is certified that error appears in the above-identified patent and that said Letters Patent is hereby corrected as shown below:

Column 33, line 36, "...1oxopropoxy)..." should be -- ... 1-oxopropoxy)... --

Column 33, line 38, "...2(R)(3..." should be -- ...2(R)-(3... --

Column 34, line 10, "thienylethio" should be --thienylthio--

Column 34, line 39, "(Cyclopentylthio)2" should be -- (Cyclopentylthio)-2 --

Column 34, line 43, "3-1-Ethylpropylthio)" should be -- 3-((1-Ethylpropyl)thio) --

Signed and Sealed this

Twenty-seventh Day of December, 1994

Attest:

BRUCE LEHMAN

*Attesting Officer*   *Commissioner of Patents and Trademarks*